(12) United States Patent
Schymkowitz et al.

(10) Patent No.: US 9,095,556 B2
(45) Date of Patent: *Aug. 4, 2015

(54) METHOD FOR INDUCING PROTEIN AGGREGATION USING A POLYPEPTIDE WITH AN AGGREGATION REGION

(75) Inventors: Joost Schymkowitz, Meensel-Kiezegem (BE); Frederic Rousseau, Groot-Bijgaarden (BE)

(73) Assignees: VIB VZW, Zwijnaarde (BE); VRIJE UNIVERSITEIT BRUSSEL, Brussels (BE)

( * ) Notice: Subject to any disclaimer, the term of this patent is extended or adjusted under 35 U.S.C. 154(b) by 574 days.

This patent is subject to a terminal disclaimer.

(21) Appl. No.: 12/214,761

(22) Filed: Jun. 20, 2008

(65) Prior Publication Data

US 2009/0012275 A1  Jan. 8, 2009

Related U.S. Application Data

(63) Continuation of application No. PCT/EP2006/070184, filed on Dec. 22, 2006.

(60) Provisional application No. 60/753,245, filed on Dec. 22, 2005, provisional application No. 60/872,079, filed on Dec. 1, 2006.

(30) Foreign Application Priority Data

Dec. 22, 2005  (EP) .................................... 05112761
Dec. 1, 2006  (EP) .................................... 06125189

(51) Int. Cl.
| A61K 38/00 | (2006.01) |
|---|---|
| A61K 38/16 | (2006.01) |
| A61K 38/10 | (2006.01) |
| A61K 38/08 | (2006.01) |
| A61K 38/18 | (2006.01) |
| A61K 47/48 | (2006.01) |
| C12N 15/82 | (2006.01) |

(52) U.S. Cl.
CPC ............. *A61K 38/1866* (2013.01); *A61K 38/16* (2013.01); *A61K 47/48246* (2013.01); *C12N 15/8216* (2013.01); *C12N 15/8257* (2013.01); *C07K 2319/735* (2013.01)

(58) Field of Classification Search
None
See application file for complete search history.

(56) References Cited

U.S. PATENT DOCUMENTS

| 4,186,183 A | 1/1980 | Steck et al. |
|---|---|---|
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,550,017 A | 10/1985 | Liu et al. |
| 4,774,085 A | 9/1988 | Fidler |
| 4,797,368 A | 1/1989 | Carter et al. |
| 4,837,028 A | 6/1989 | Allen |
| 4,897,355 A | 1/1990 | Eppstein et al. |
| 4,946,787 A | 8/1990 | Eppstein et al. |
| 5,049,386 A | 9/1991 | Eppstein et al. |
| 5,173,414 A | 12/1992 | Lebkowski et al. |
| 6,159,748 A | 12/2000 | Hechinger |
| 6,399,317 B1 | 6/2002 | Weimer |
| 6,489,092 B1 | 12/2002 | Benjamin et al. |
| 6,627,616 B2 | 9/2003 | Monahan et al. |
| 6,682,940 B2 | 1/2004 | Pankowsky |
| 2002/0098173 A1* | 7/2002 | Findeis et al. ............... 424/94.3 |
| 2005/0026165 A1 | 2/2005 | Orser et al. |
| 2005/0203010 A1* | 9/2005 | Kim ............................... 514/12 |

FOREIGN PATENT DOCUMENTS

| WO | WO 91/16024 | 10/1991 |
|---|---|---|
| WO | WO 91/17424 | 11/1991 |
| WO | WO 93/24641 | 12/1993 |
| WO | WO 03/102187 A1 | 12/2003 |
| WO | WO 2004/009625 A2 * | 1/2004 |
| WO | WO 2007/071789 A1 | 6/2007 |

OTHER PUBLICATIONS

Kizana et al., Heart, Lung and Circulation 2007;16:180-184.*
Lee et al., Prot. Express. Purif. 40:183-189, 2005.*
Yudt et al., Steroids 66:549-558, 2001.*
Chi et al., Pharmaceutical Res. 20:1326-1336, 2003.*
Prasanna et al., Biochemistry 37:6883-6893, 1998.*
Terpe, K., Appl. Microbiol. Biotechnol. 60:523-533, 2003.*
Blum et al., PNAS 97:2241-2246, 2000.*
Linding et al., J. Mol. Biol. 342:345-353, 2004.*
PCT International Search Report, PCT/EP2006/070184, dated Mar. 16, 2007.
Fernandez-Escamilla et al., "Prediction of sequence-dependent and mutational effects on the aggregation of peptides and proteins," *Nature Biotechnology*, vol. 22, No. 10, pp. 1302-1306, Oct. 2004.
Bairoch et al., "The Universal Protein Resource (UniProt)," *Nucleic Acids Research*, vol. 33, Database issue, D154-D159, 2005.
Barral et al., "Roles of molecular chaperones in protein misfolding diseases," *Seminars in Cell & Developmental Biology*, vol. 15, pp. 17-29, 2004.
Chiti et al., "Rationalization of the effects of mutations on peptide and protein aggregation rates," *Nature*, vol. 424, pp. 805-808, Aug. 14, 2003.
Clark, "Protein aggregation determinants from a simplified model: Cooperative folders resist aggregation," *Protein Science*, vol. 14, pp. 653-662, 2005.
De Marco et al., "The solubility and stability of recombinant proteins are increased by their fusion to NusA," *Biochemical and Biophysical Research Communications*, vol. 322, pp. 766-771, 2004.
Dobson, "Getting out of shape," *Nature*, vol. 418, pp. 729-730, Aug. 15, 2002.

(Continued)

*Primary Examiner* — David J Steadman
(74) *Attorney, Agent, or Firm* — Foley & Lardner LLP

(57) ABSTRACT

The invention belongs to the field of functional proteomics and, more particularly, to the field of protein aggregation. Described are methods for interfering with the function of a target protein and uses a non-naturally, user-designed molecule, designated as interferor, that has a specificity for a target protein and that induces aggregation upon contact with the target protein. The invention also discloses such interferer molecules and their use in therapeutic applications.

11 Claims, 2 Drawing Sheets

(56) References Cited

OTHER PUBLICATIONS

Dobson, "Principles of protein folding, misfolding and aggregation," *Seminars in Cell & Developmental Biology*, vol. 15, pp. 3-16, 2004.
Guex et al., "Swiss-Model and the Swiss-Pdb Viewer: An environment for comparative protein modeling," *Electrophoresis*, vol. 18. pp. 2714-2723, 1997.
Pawar et al., "Prediction of "Aggregation-prone" and "Aggregation-susceptible" Regions in Proteins Associated with Neurodegenerative Diseases," *J. Mol. Biol.*, vol. 350, pp. 379-392, 2005.
Hamada et al., "Engineering amyloidogenicity towards the development of nanofibrillar materials," *Trends in Biotechnology*, vol. 22, No. 2, pp. 93-97, Feb. 2004.
Houry et al., "Identification of in vivo substrates of the chaperonin GroEL," *Nature*, vol. 402, pp. 147-154, Nov. 11, 1999.
Kopp et al., "The Swiss-Model Repository of annotated three-dimensional protein structure homology models," *Nucleic Acids Research*, vol. 32, Database issue, pp. D230-D234, 2004.
Linding et al., "A Comparative Study of the Relationship Between Protein Structure and β-Aggregation in Globular and Intrinsically Disordered Proteins," *J. Mol. Biol.*, vol. 342, pp. 345-353, 2004.
López De La Paz et al., "Sequence determinants of amyloid fibril formation," *PNAS*, vol. 101, No. 1, pp. 87-92, Jan. 6, 2004.
Makin et al., "Molecular basis for amyloid fibril formation and stability," *PNAS*, vol. 102, No. 2, pp. 315-320, Jan. 11, 2005.
Nelson et al., "Structure of the cross-β spine of amyloid-like fibrils," *Nature*, vol. 435, pp. 773-778, Jun. 2005.
Barelle et al., "GFP as a quantitative reporter of gene regulation in *Candida albicans*," *Yeast*, vol. 21, pp. 333-340, 2004.
Leuker et al., "Sequence and promoter regulation of the *PCK1* gene encoding phosphoenolpyruvate carboxykinase of the fungal pathogen *Candida albicans*," *Gene*, vol. 192, pp. 235-240, 1997.
Fonzi et al., "Isogenic Strain Construction and Gene Mapping in *Candida albicans*," *Genetics*, vol. 134, pp. 717-728, Jul. 1993.
Yoon et al., "Detecting hidden sequence propensity for amyloid fibril formation," *Protein Science*, vol. 13, pp. 2149-2160, 2004.
Esteras-Chopo et al., "The amyloid stretch hypothesis: Recruiting proteins toward the dark side," *PNAS*, vol. 102, No. 46, pp. 16672-16677, Nov. 15, 2005.
Sánchez De Groot et al., "Prediction of "hot spots" of aggregation in disease-linked polypeptides," *BMC Structural Biology*, vol. 5, No. 18, pp. 1-15, Sep. 30, 2005.
Tartaglia et al., "Prediction of aggregation rate and aggregation-prone segments in polypeptide sequences," *Protein Science*, vol. 14, pp. 2723-2734, 2005.
Ventura et al., "Short amino acid stretches can mediate amyloid formation in globular proteins: The Src homology 3 (SH3) case," *PNAS*, vol. 101, No. 19, pp. 7258-7263, May 11, 2004.

\* cited by examiner

SEQUENCE LISTING

<160> NUMBER OF SEQ ID NOS: 59

<210> SEQ ID NO 1
<211> LENGTH: 22
<212> TYPE: PRT
<213> ORGANISM: Artificial Sequence
<220> FEATURE:
<223> OTHER INFORMATION: Synthetic peptide

<400> SEQUENCE: 1

Ser Thr Leu Ile Val Leu Gln Asn Ser Thr Val Ile Phe Glu Gln Asn
1               5                   10                  15

Ser Thr Val Ile Phe Glu
            20

<210> SEQ ID NO 2
<211> LENGTH: 6
<212> TYPE: PRT
<213> ORGANISM: Artificial Sequence
<220> FEATURE:
<223> OTHER INFORMATION: Synthetic hexapeptide

<400> SEQUENCE: 2

Ser Thr Leu Ile Val Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Flexible linker sequence

<400> SEQUENCE: 3

Lys Pro Gly Ala Ala Lys Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Self-association sequence

<400> SEQUENCE: 4

Gly Val Val Leu Val Thr Ser Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Self-association sequence

<400> SEQUENCE: 5

Leu Leu Leu Thr Thr Tyr Phe
1               5

<210> SEQ ID NO 6
<211> LENGTH: 5
<212> TYPE: PRT
<213> ORGANISM: Artificial Sequence
<220> FEATURE:
<223> OTHER INFORMATION: Self-association sequence

<400> SEQUENCE: 6

```
Leu Thr Leu Leu Val
1               5

<210> SEQ ID NO 7
<211> LENGTH: 5
<212> TYPE: PRT
<213> ORGANISM: Artificial Sequence
<220> FEATURE:
<223> OTHER INFORMATION: Self-association sequence

<400> SEQUENCE: 7

Leu Ala Phe Ile Gly
1               5

<210> SEQ ID NO 8
<211> LENGTH: 16
<212> TYPE: PRT
<213> ORGANISM: Escherichia coli

<400> SEQUENCE: 8

Asp Tyr Asp Leu Glu Ala Leu Ala Phe Ile Gly Lys Gln Gln Glu Glu
1               5                   10                  15

<210> SEQ ID NO 9
<211> LENGTH: 23
<212> TYPE: PRT
<213> ORGANISM: Homo sapiens

<400> SEQUENCE: 9

Ile Ile Val Ala Val Val Ile Ala Thr Ala Val Ala Ala Ile Val Ala
1               5                   10                  15

Ala Val Val Ala Leu Ile Tyr
            20

<210> SEQ ID NO 10
<211> LENGTH: 10
<212> TYPE: PRT
<213> ORGANISM: Homo sapiens

<400> SEQUENCE: 10

Leu Thr Val Leu Leu Leu Leu Ala Ser Ala
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Linker sequence

<400> SEQUENCE: 11

Ala Asp Pro Arg Gly Ala Ala Glu Gly Ala
1               5                   10

<210> SEQ ID NO 12
<211> LENGTH: 20
<212> TYPE: PRT
<213> ORGANISM: Artificial Sequence
<220> FEATURE:
<223> OTHER INFORMATION: Designed sequence

<400> SEQUENCE: 12

Ala Asp Pro Arg Gly Ala Ala Glu Gly Ala Ile Ile Val Ala Val Val
1               5                   10                  15
```

```
Ile Ala Thr Ala
            20

<210> SEQ ID NO 13
<211> LENGTH: 20
<212> TYPE: PRT
<213> ORGANISM: Artificial Sequence
<220> FEATURE:
<223> OTHER INFORMATION: Designed sequence

<400> SEQUENCE: 13

Ala Asp Pro Arg Gly Ala Ala Glu Gly Ala Val Val Ile Ala Thr Ala
1               5                   10                  15

Val Ala Ala Ile
            20

<210> SEQ ID NO 14
<211> LENGTH: 20
<212> TYPE: PRT
<213> ORGANISM: Artificial Sequence
<220> FEATURE:
<223> OTHER INFORMATION: Designed sequence

<400> SEQUENCE: 14

Ala Asp Pro Arg Gly Ala Ala Glu Gly Ala Ile Val Ala Ala Val Val
1               5                   10                  15

Ala Leu Ile Tyr
            20

<210> SEQ ID NO 15
<211> LENGTH: 20
<212> TYPE: PRT
<213> ORGANISM: Artificial Sequence
<220> FEATURE:
<223> OTHER INFORMATION: Designed sequence

<400> SEQUENCE: 15

Ala Asp Pro Arg Gly Ala Ala Glu Gly Ala Leu Thr Val Leu Leu Leu
1               5                   10                  15

Leu Ala Ser Ala
            20

<210> SEQ ID NO 16
<211> LENGTH: 8
<212> TYPE: PRT
<213> ORGANISM: Sus barbatus

<400> SEQUENCE: 16

Ala Leu Phe Trp Leu Leu Val Thr
1               5

<210> SEQ ID NO 17
<211> LENGTH: 9
<212> TYPE: PRT
<213> ORGANISM: Escherichia coli

<400> SEQUENCE: 17

Ala Val Ile Ile Trp Ser Leu Gly Asn
1               5

<210> SEQ ID NO 18
<211> LENGTH: 7
<212> TYPE: PRT
<213> ORGANISM: Escherichia coli
```

```
<400> SEQUENCE: 18

Ala Leu Ala Val Val Leu Gln
1               5

<210> SEQ ID NO 19
<211> LENGTH: 12
<212> TYPE: PRT
<213> ORGANISM: Leuconostoc mesenteroides

<400> SEQUENCE: 19

Ala Phe Val Asp Ala Ile Ser Ala Val Tyr Thr Ala
1               5                   10

<210> SEQ ID NO 20
<211> LENGTH: 29
<212> TYPE: PRT
<213> ORGANISM: Artificial Sequence
<220> FEATURE:
<223> OTHER INFORMATION: Interferor molecule

<400> SEQUENCE: 20

Arg Glu Ala Gly Phe Leu Leu Ser Trp Val His Trp Thr Leu Ala Leu
1               5                   10                  15

Leu Leu Tyr Leu His His Gly Gly Glu Glu Arg Ala Gly
            20                  25

<210> SEQ ID NO 21
<211> LENGTH: 4
<212> TYPE: PRT
<213> ORGANISM: Artificial Sequence
<220> FEATURE:
<223> OTHER INFORMATION: Solubilizing region

<400> SEQUENCE: 21

Arg Glu Ala Gly
1

<210> SEQ ID NO 22
<211> LENGTH: 7
<212> TYPE: PRT
<213> ORGANISM: Artificial Sequence
<220> FEATURE:
<223> OTHER INFORMATION: Solubilizing region

<400> SEQUENCE: 22

Gly Gly Glu Glu Arg Ala Gly
1               5

<210> SEQ ID NO 23
<211> LENGTH: 44
<212> TYPE: PRT
<213> ORGANISM: Artificial Sequence
<220> FEATURE:
<223> OTHER INFORMATION: Interferor molecule

<400> SEQUENCE: 23

Ser Thr Val Ile Ile Glu Gly Gly Ala Gly Asn His Val Thr Leu Ser
1               5                   10                  15

Gly Gly Ala Gly Gln Phe Leu Leu Ser Trp Val His Trp Thr Leu Ala
            20                  25                  30

Leu Leu Leu Tyr Leu His His Gly Glu Arg Ala Gly
        35                  40

<210> SEQ ID NO 24
```

```
<211> LENGTH: 5
<212> TYPE: PRT
<213> ORGANISM: Artificial Sequence
<220> FEATURE:
<223> OTHER INFORMATION: Solubilizing region

<400> SEQUENCE: 24

Gly Glu Arg Ala Gly
1               5

<210> SEQ ID NO 25
<211> LENGTH: 6
<212> TYPE: PRT
<213> ORGANISM: Artificial Sequence
<220> FEATURE:
<223> OTHER INFORMATION: Self-association region

<400> SEQUENCE: 25

Ser Thr Val Ile Ile Glu
1               5

<210> SEQ ID NO 26
<211> LENGTH: 4
<212> TYPE: PRT
<213> ORGANISM: Artificial Sequence
<220> FEATURE:
<223> OTHER INFORMATION: Linker

<400> SEQUENCE: 26

Gly Gly Ala Gly
1

<210> SEQ ID NO 27
<211> LENGTH: 6
<212> TYPE: PRT
<213> ORGANISM: Artificial Sequence
<220> FEATURE:
<223> OTHER INFORMATION: Self-association region

<400> SEQUENCE: 27

Asn His Val Thr Leu Ser
1               5

<210> SEQ ID NO 28
<211> LENGTH: 5
<212> TYPE: PRT
<213> ORGANISM: Artificial Sequence
<220> FEATURE:
<223> OTHER INFORMATION: Linker

<400> SEQUENCE: 28

Gly Gly Ala Gly Gln
1               5

<210> SEQ ID NO 29
<211> LENGTH: 18
<212> TYPE: PRT
<213> ORGANISM: Mus musculus

<400> SEQUENCE: 29

Phe Leu Leu Ser Trp Val His Trp Thr Leu Ala Leu Leu Leu Tyr Leu
1               5                   10                  15

His His

<210> SEQ ID NO 30
<211> LENGTH: 33
```

```
<212> TYPE: PRT
<213> ORGANISM: Artificial Sequence
<220> FEATURE:
<223> OTHER INFORMATION: Interferor molecule

<400> SEQUENCE: 30

Ser Thr Val Ile Ile Glu Gly Gly Ala Gly Phe Leu Leu Ser Trp Val
1               5                   10                  15

His Trp Thr Leu Ala Leu Leu Leu Tyr Leu His His Gly Glu Arg Ala
            20                  25                  30

Gly

<210> SEQ ID NO 31
<211> LENGTH: 8
<212> TYPE: PRT
<213> ORGANISM: Homo sapiens

<400> SEQUENCE: 31

Ile Leu Thr Ile Ile Thr Leu Glu
1               5

<210> SEQ ID NO 32
<211> LENGTH: 9
<212> TYPE: PRT
<213> ORGANISM: Homo sapiens

<400> SEQUENCE: 32

Met Ile Leu Thr Val Phe Leu Ser Asn
1               5

<210> SEQ ID NO 33
<211> LENGTH: 10
<212> TYPE: PRT
<213> ORGANISM: Danio rerio

<400> SEQUENCE: 33

Phe Leu Ala Ala Leu Leu His Leu Ser Ala
1               5                   10

<210> SEQ ID NO 34
<211> LENGTH: 20
<212> TYPE: PRT
<213> ORGANISM: Artificial Sequence
<220> FEATURE:
<223> OTHER INFORMATION: Interferor molecule

<400> SEQUENCE: 34

Arg Leu Phe Leu Ala Ala Leu Leu Arg Phe Leu Ala Ala Leu Leu His
1               5                   10                  15

Leu Ser Ala Arg
            20

<210> SEQ ID NO 35
<211> LENGTH: 20
<212> TYPE: PRT
<213> ORGANISM: Artificial Sequence
<220> FEATURE:
<223> OTHER INFORMATION: Interferor molecule

<400> SEQUENCE: 35

Arg Phe Leu Ala Ala Leu Leu His Leu Ser Ala Arg Leu Phe Leu Ala
1               5                   10                  15

Ala Leu Leu Arg
            20
```

<210> SEQ ID NO 36
<211> LENGTH: 18
<212> TYPE: PRT
<213> ORGANISM: Artificial Sequence
<220> FEATURE:
<223> OTHER INFORMATION: Interferor molecule

<400> SEQUENCE: 36

Arg Tyr Leu Ala Ile Leu Ala Gly Ile Arg Leu Phe Leu Ala Ala Leu
1               5                   10                  15

Leu Arg

<210> SEQ ID NO 37
<211> LENGTH: 21
<212> TYPE: PRT
<213> ORGANISM: Artificial Sequence
<220> FEATURE:
<223> OTHER INFORMATION: Interferor molecule

<400> SEQUENCE: 37

Arg Tyr Leu Ala Ile Leu Ala Gly Ile Arg Phe Leu Ala Ala Leu Leu
1               5                   10                  15

His Leu Ser Ala Arg
            20

<210> SEQ ID NO 38
<211> LENGTH: 13
<212> TYPE: PRT
<213> ORGANISM: Danio rerio

<400> SEQUENCE: 38

Glu Ala Leu Val Val Tyr Leu Ile Gln Leu Ala Gly Arg
1               5                   10

<210> SEQ ID NO 39
<211> LENGTH: 7
<212> TYPE: PRT
<213> ORGANISM: Saccharomyces cerevisiae

<400> SEQUENCE: 39

Val Ile Gly Phe Ile Ala Gln
1               5

<210> SEQ ID NO 40
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 40
cctctagaat gaaagaaatt ttggctgtag                                       30

<210> SEQ ID NO 41
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 41
ccgtcgactt aagcttgagc aataaagccg ataacgccag cagcgcccgg tttagcagc       59

```
<210> SEQ ID NO 42
<211> LENGTH: 8
<212> TYPE: PRT
<213> ORGANISM: Candida albicans

<400> SEQUENCE: 42

Val Ile Ser Val Ala Val Ser Leu
1               5

<210> SEQ ID NO 43
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 43
attgtacaaa tatccgtatg tgcctgacta cgcaatggct cagtggcaga ac            52

<210> SEQ ID NO 44
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 44
gcgctagctt aagctaggga tacagcgact gagatgacgc cagcagcgcc cggttta       57

<210> SEQ ID NO 45
<211> LENGTH: 15
<212> TYPE: PRT
<213> ORGANISM: Arabidopsis thaliana

<400> SEQUENCE: 45

Val Phe Trp Leu Ile Leu Phe Ser Gly Leu Leu Val Ile Thr Leu
1               5                   10                  15

<210> SEQ ID NO 46
<211> LENGTH: 22
<212> TYPE: PRT
<213> ORGANISM: Arabidopsis thaliana

<400> SEQUENCE: 46

Ile Ile Ile Ala Val Val Val Thr Ala Val Ser Thr Phe Leu Leu Ala
1               5                   10                  15

Ala Leu Phe Phe Leu Cys
            20

<210> SEQ ID NO 47
<211> LENGTH: 14
<212> TYPE: PRT
<213> ORGANISM: Arabidopsis thaliana

<400> SEQUENCE: 47

Phe Phe Phe Phe Tyr Ile Phe Phe Ser Val Ser Val Ser Ser
1               5                   10

<210> SEQ ID NO 48
<211> LENGTH: 22
<212> TYPE: PRT
<213> ORGANISM: Arabidopsis thaliana

<400> SEQUENCE: 48

Ala Ile Val Ile Ser Val Gly Ile Val Thr Leu Gly Met Leu Ser Ala
```

```
1               5                   10                  15

Leu Ala Phe Phe Leu Tyr
            20

<210> SEQ ID NO 49
<211> LENGTH: 6
<212> TYPE: PRT
<213> ORGANISM: Arabidopsis thaliana

<400> SEQUENCE: 49

Gln Phe Ile Val Val Met
1               5

<210> SEQ ID NO 50
<211> LENGTH: 7
<212> TYPE: PRT
<213> ORGANISM: Arabidopsis thaliana

<400> SEQUENCE: 50

Tyr Leu Ile Leu Glu Tyr Ala
1               5

<210> SEQ ID NO 51
<211> LENGTH: 5
<212> TYPE: PRT
<213> ORGANISM: Arabidopsis thaliana

<400> SEQUENCE: 51

Tyr Gly Tyr Phe Tyr
1               5

<210> SEQ ID NO 52
<211> LENGTH: 11
<212> TYPE: PRT
<213> ORGANISM: Arabidopsis thaliana

<400> SEQUENCE: 52

Val Tyr Leu Ile Leu Glu Tyr Ala Val Arg Gly
1               5                   10

<210> SEQ ID NO 53
<211> LENGTH: 5
<212> TYPE: PRT
<213> ORGANISM: Arabidopsis thaliana

<400> SEQUENCE: 53

Ile Phe Leu Ile Leu
1               5

<210> SEQ ID NO 54
<211> LENGTH: 4
<212> TYPE: PRT
<213> ORGANISM: Arabidopsis thaliana

<400> SEQUENCE: 54

Phe Gly Trp Phe
1

<210> SEQ ID NO 55
<211> LENGTH: 9
<212> TYPE: PRT
<213> ORGANISM: Arabidopsis thaliana

<400> SEQUENCE: 55
```

```
Ser Ile Ile Ala Ile Leu Thr Leu Trp
1               5

<210> SEQ ID NO 56
<211> LENGTH: 11
<212> TYPE: PRT
<213> ORGANISM: Arabidopsis thaliana

<400> SEQUENCE: 56

Gly Phe Trp Val Gln Val Leu Tyr Tyr Pro Phe
1               5                   10

<210> SEQ ID NO 57
<211> LENGTH: 5
<212> TYPE: PRT
<213> ORGANISM: Arabidopsis thaliana

<400> SEQUENCE: 57

Ile Trp Thr Ile Ala
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic peptide

<400> SEQUENCE: 58

Ser Thr Leu Ile Val Leu
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic peptide

<400> SEQUENCE: 59

Ser Thr Val Ile Phe Glu
1               5
```

METHOD FOR INDUCING PROTEIN AGGREGATION USING A POLYPEPTIDE WITH AN AGGREGATION REGION

CROSS-REFERENCE TO RELATED APPLICATIONS

This application is a continuation of PCT International Patent Application No. PCT/EP2006/070184, filed on Dec. 22, 2006, designating the United States of America, and published, in English, as PCT International Publication No. WO 2007/071789 A1 on Jun. 28, 2007. PCT/EP2006/070184 claims priority to European Patent Application Serial No. 06125189.8 and U.S. Provisional Patent Application Ser. No. 60/872,079, both filed on Dec. 1, 2006, and European Patent Application Serial No. 05112761.1 and U.S. Provisional Patent Application Ser. No. 60/753,245, both filed on Dec. 22, 2005, the contents of the entirety of each of which are hereby incorporated herein by this reference. This application claims priority under 35 U.S.C. §119(e) to both said U.S. Provisional Patent Application Ser. No. 60/872,079, both filed on Dec. 1, 2006, and U.S. Provisional Patent Application Ser. No. 60/753,245, both filed on Dec. 22, 2005.

STATEMENT ACCORDING to 37 C.F.R §1.52(e)(5)—

SEQUENCE LISTING SUBMITTED on COMPACT DISC

Pursuant to 37 C.F.R. §1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "New Seq Listing_ST25.txt" that is 27 KB and created on Jun. 18, 2008.

TECHNICAL FIELD

The invention belongs to the field of functional proteomics and, more particularly, to the field of protein aggregation. Disclosed are methods for interfering with the function of a target protein and uses a non-naturally, user-designed molecule, designated as "interferer", that has a specificity for a target protein and that induces aggregation upon contact with the target protein. Also disclosed are such interferer molecules and their use in therapeutic applications.

BACKGROUND

Biology is entering an exciting era brought about by the increase in genome-wide information. As genome sequencing and high-throughput functional genomics approaches generate more and more data, researchers need new ways to tease out biologically relevant information. Functional genomics in particular is making rapid progress in assigning biological meaning to genomic data. The information encoded in the genome comprises genes, the protein products of which mediate most of the functions in organisms, and control elements. Proteins were thought to be the most important effectors in the cells, although recently non-coding RNAs have also been identified as important players in regulatory processes.

Several key biological questions are central to continuing genome projects and are relevant to any cellular organism, from bacteria to humans. One challenge is to understand how genes that are encoded in a genome operate and interact to produce a complex living system. A related challenge is to determine the function of all the sequence elements in the genome. The toolbox of functional genomics has enabled several systematic approaches that can provide the answers to a few basic questions for the majority of genes in a genome, including when is a gene expressed, where its product is localized, which other gene products does it interact with and what phenotype results if a gene is mutated. Phenotypic analysis of mutants has been a powerful approach for determining gene function. Gene function can be altered through gene deletions, insertional mutagenesis and RNA interference (RNAi). RNAi is a relatively recent development for reducing gene expression. It follows reports of gene silencing in plants and other model organisms, and is based on the observation from *C. elegans* that adding double-stranded RNA (dsRNA) to cells often interferes with gene function in a sequence-specific manner. In many cases, the level of functional reduction cannot be adequately controlled, is incomplete, the level of specificity is not entirely predictable and in some organisms RNAi does not work (e.g., in the yeast *Candida albicans*).

Functional genomics has changed the way biology is done, and yet, the field is still in its infancy in terms of detailing the complexity that underlies biological systems, such as the complex network of genetic regulation, protein interactions and biochemical reactions that make up a cell.

The conversion of normally soluble proteins into conformationally altered insoluble proteins is thought to be a causative process in a variety of diseases, such as, for example, the occurrence of amyloid beta peptide in Alzheimer's disease and cerebral amyloid angiopathy, alpha-synuclein deposits in Lewy bodies of Parkinson's disease, prions in Creutzfeldt-Jacob disease, superoxide dismutase in amyotrophic lateral sclerosis and tau in neurofibrillary tangles in frontal temporal dementia and Pick's disease. Thus far, protein aggregation has mainly been studied as an unwanted, disease-causing phenomenon, and it is widely accepted that cross-beta-mediated aggregation is the most frequently occurring and biologically relevant mechanism of aggregation.[2]

"Cross-beta aggregation" is the term used to indicate that aggregation is nucleated via the formation of intermolecular beta-sheets to which each molecule in the aggregate contributes an identical strand typically comprising at least three contiguous amino acids. There is now abundant data to show that the individual strands interact to form an intermolecular beta sheet and that this structure forms the backbone of the aggregate.[3,4]

Self-association regions in target proteins can be determined by computer programs, such as TANGO,[6] which were developed for predicting the aggregation propensity of peptides and proteins. One specific form of aggregation, namely the highly ordered amyloid fiber, is already being explored in the art for potential use in the material sciences.[5] In addition, WO03102187 (Scegen, Pty Ltd), the contents of which are incorporated herein by this reference, discloses a method for enhancing the activity of a molecule by fusing the molecule with a membrane translocating sequence, whereby the resulting chimeric molecule self-assembles into a higher molecular weight aggregate. U.S. 20050026165 (Areté Associates), the contents of which are incorporated herein by this reference, discloses the use of conformational peptides, able to interact with the beta-sheet conformation of insoluble proteins such as prions, as a diagnostic tool for prion diseases.

DISCLOSURE OF THE INVENTION

Provided is a technology for the controlled and inducible protein aggregation of specific target proteins. Also provided are de novo designed molecules, herein designated as interferer molecules, which comprise at least one aggregation region of which the aggregation region is derived from a target protein. In certain embodiments, the interferer molecule comprises at least one self-association region that is fused to a moiety that prevents aggregation of the self-association region. Upon contact between a chosen target protein and a specifically designed interferer molecule, a specific co-aggregation occurs between the target and the interferor, resulting in a functional knock-out or a down-regulation of the biological function for the target protein. This protein knock-down is conditional upon the presence of aggregates, which are induced by the presence of the interferer molecule. An additional advantage is that the strength of the protein interference can be experimentally controlled by varying the number of aggregation regions in the interferor molecule. Not only provided is an efficient tool to down-regulate the biological function of a specific extra- or intracellular protein, but also important therapeutic, agricultural and diagnostic applications.

DETAILED DESCRIPTION OF THE INVENTION

Figure 1:
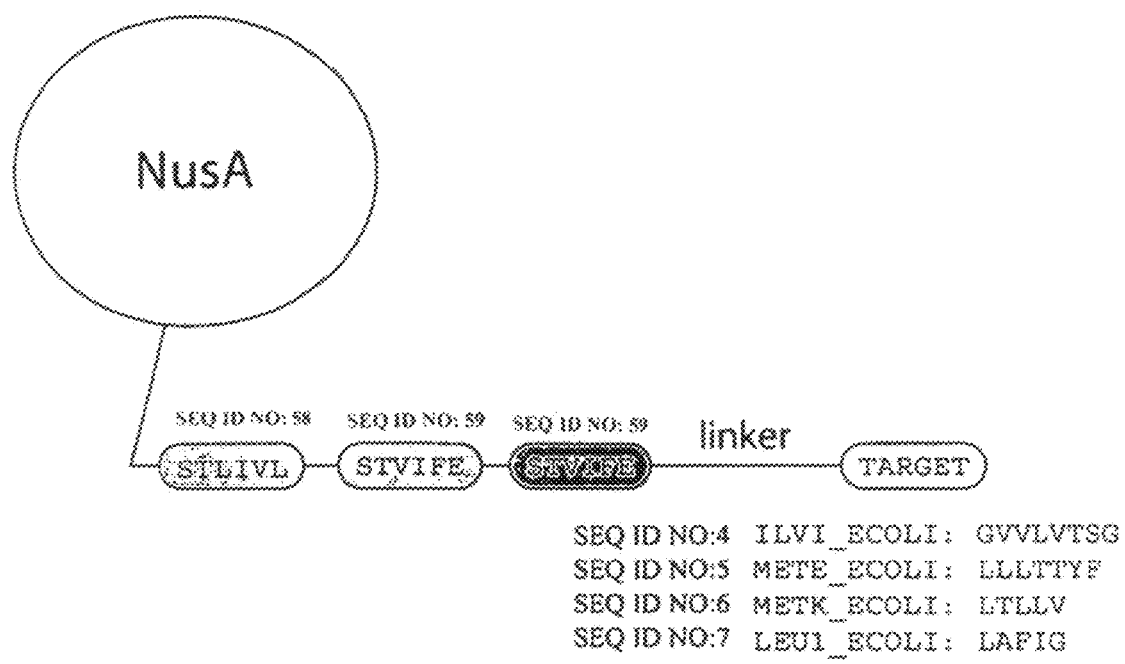
FIG. 1: Protein interference in *E. coli* using recombinant expression of four different interferer constructs that target specific enzymes involved in amino acid biosynthesis. Part B of each interferor molecule consists of three synthetic self-association sequences, separated by linkers of two amino acids and one specific self-associating region derived from the enzyme. The self-association regions (synthetic and specific) are coupled to the protein NusA, which serves as a moiety to prevent aggregation (id est part A of the interferer molecule) of the self-association regions.

Described are processes for down-regulating the biological function of a protein through the use of interferer molecules having a specificity for a target protein. Upon contact with a target protein, a co-aggregation occurs between the interferer molecule and the target. The aggregation withdraws the target from its soluble environment and results in a functional knock-down of the target protein.

Thus, in certain embodiments, provided are methods for down-regulating the biological function of a protein, such a method comprising contacting the protein with a non-naturally occurring molecule comprising at least one self-association region isolated from the protein.

In another embodiment, provided are methods for down-regulating the biological function of a protein, the method comprising contacting the protein with a non-naturally occurring molecule consisting of at least one self-association region isolated from the protein.

In certain embodiments, provided are methods for down-regulating the biological function of a protein, such a method comprising contacting the protein with a non-naturally occurring molecule comprising at least one self-association region isolated from the protein, wherein the self-association domain is fused to a moiety that prevents aggregation of the self-association region.

In certain embodiments, provided are methods for down-regulating the biological function of a protein, such a method comprising contacting the protein with a non-naturally occurring molecule consisting of at least one self-association region isolated from the protein wherein the self-association domain is fused to a moiety that prevents aggregation of the self-association region.

In certain embodiments, provided are methods for down-regulating the biological function of a protein, such a method comprising contacting the protein with a non-naturally occurring molecule that comprises part A and part B, wherein i) part A is a peptide or a protein domain or an agarose bead preventing aggregation of part B, and ii) part B, which comprises at least one self-association region consisting of at least three contiguous amino acids, and wherein the region is isolated from the protein, which function is to be down-regulated with, and wherein a linker is optionally present between parts A and B.

In certain embodiments, provided are methods for down-regulating the function of a protein, such a method comprising contacting the protein with a non-naturally occurring molecule that comprises part A and part B, wherein i) part A is a peptide or a protein domain or an agarose bead preventing aggregation of part B so that part B is in direct contact with the solvent, wherein the molecule and the protein are present, and ii) part B, which comprises at least one self-association region, wherein the region consists of at least three contiguous amino acids and wherein the region is isolated from the protein, which function is to be down-regulated with, and wherein a linker is optionally present between parts A and B.

In certain embodiments, part B of the non-naturally occurring molecule comprises at least two self-association regions, wherein at least one of the regions is derived from the protein, which function is to be interfered with.

The term "non-naturally occurring molecule" refers to the fact that such an interferor molecule is manmade. For instance, when an interferor molecule is polypeptide (id est both parts A and B are peptides) such polypeptide is designed by isolating part B from a target protein (id est the self-association region) and by coupling the part B to a part A, which can be derived (i) from another protein or (ii) from the same target protein, in which case, the part A is not present immediately adjacent to part B. In other words, the self-association region derived from the target fused to a moiety (when the interferer is a polypeptide, the moiety is also a polypeptide) that prevents the aggregation of the self-association region is different from a naturally occurring fusion between parts A and B by at least one natural amino acid. Typically, such interferer molecule will not exist as a contiguous polypeptide in a protein encoded by a gene in a non-recombinant genome.

Interferor molecules can be designed in a modular fashion, by introducing repetition and changing the order of parts A and B. A non-limiting list of the following combinations is: an interferer with the A-B—structure, an interferer with the B-A—structure, an interferer with the A-B-A—structure, an interferer with the B-A-B—structure, an interferer with the A'-B-A" structure and an interferer with the B'-A-B" structure, wherein a linker (spacer) is optionally present between parts A, A', A" and B, B', B". A, A' and A" are different of similar moieties (e.g., different peptide sequences). B, B' and B" are different or similar self-association sequences (e.g., B is a self-association sequence derived from the target protein and B' is a synthetic self-association sequence).

In still other words, provided is a method for down-regulating the biological function of a protein comprising contacting the protein with a molecule comprising at least one self-association region isolated from the protein, wherein the self-association region is fused to a moiety that prevents aggregation of the self-association region so that the self-association region is in direct contact with the solvent, wherein the molecule and the protein are present.

From the foregoing, it should be clear that the "moiety" is equivalent with the term part A and part B is equivalent with the wording "at least one self-association region."

The wording "down-regulating the function of a protein" means that the normal biological activity of a protein is reduced (inhibited, down-regulated, reduced and disrupted are equivalent words here) or that the protein is withdrawn from its normal biological environment (e.g., a protein that is a normal resident of the endoplasmic reticulum is not present through down-regulation of its function). Thus, by applying the method of the invention, the function of a protein is disrupted through an aggregation of the protein by contacting the protein with the non-natural molecule of the invention. The non-natural molecule is herein designated as "the interferer" or the "interferer molecule." Aggregation refers to the fact that a protein that is normally soluble is changed into an insoluble protein or an aggregated protein in its normal biological environment through direct contact or binding with the interferor. The wording "down-regulating the function of a protein" can also be interchanged by the wording "knocking down the function of a protein" or "negatively interfering with the function of a protein."

The down-regulation of the function of a protein can also mean that a protein is not present anymore in a soluble form in the cell or that a protein is not present anymore in a soluble form in its normal biological environment (e.g., (sub)-cellular or extra-cellular localization). In addition, it can also mean that the aggregated protein is degraded through the natural clearance mechanisms of the cell and is no longer detectable in soluble or insoluble form. In addition, it can also mean that a transmembrane receptor protein cannot bind its normal ligand anymore through interferor-induced aggregation of the transmembrane protein. Thus, the down-regulation of the function of a protein can also mean that a protein that is a normal resident of, e.g., the mitochondria is not present there anymore through the method of protein interference. In certain embodiments, the "down-regulation of the function of a protein" or "the negative interference with the function of a protein" or "knocking down the function of a protein" is at least a 20%, at least a 30%, at least a 40%, at least a 50%, at least a 60%, at least a 70%, at least a 80%, at least a 90%, at least a 95% or even a 100% loss of function, as compared to the normal (100%) function of the protein.

The function of a protein or the lack of presence of a protein in its normal biological environment (localization) can conveniently be determined by methods known in the art. For example, depending on the target protein of interest, the function can be determined by measuring the reduced enzymatic activity. The reduced presence of a protein in its normal biological localization can, for example, be measured by the lack of formation of a complex, the lack of the occurrence of a target protein in a sub-cellular compartment, the presence of the target protein in soluble form, the presence of the target protein in an aggregated (insoluble is an equivalent term here) form. Alternatively, the effect of the down-regulation of a target protein can be measured in a cellular assay (e.g., loss or gain of growth, loss or gain of invasion, loss or gain of proteolytic activity).

In certain embodiments, such normal biological activity (or normal function or normal localization) of a protein can be interfered with intracellularly or extracellularly. "Intracellularly" refers to the localization of a protein inside the cell of an organism or host (e.g., the cytoplasm, the mitochondria, the lysosome, the vacuole, the nucleus, the chloroplast, the endoplasmic reticulum (ER), the cellular membrane, the mitochondrial membrane, the chloroplast membrane, etc.). "Extracellularly" not only refers to the localization of a protein in the extracellular medium of the cell, but also refers to proteins that contact the extracellular medium, such as a membrane-anchored protein, a transmembrane protein, etc. Non-limiting examples of extracellular proteins are secreted proteins (e.g., proteases, antibodies and cytokines present in the blood or plasma) or proteins present in the extracellular matrix (e.g., matrix metalloproteins and transmembrane proteins (e.g., a growth factor receptor)).

Cells or hosts that can be targeted with the method of the invention comprise prokaryotic and eukaryotic cells. Non-limiting examples are viruses, bacteria, yeasts, fungi, protozoa, plants and mammals including humans.

The method of down-regulation of the biological function of a protein can be used to interfere with the biological function with 1, 2, 3, 4, 5 or even more proteins simultaneously. Particularly, since part B comprises at least one self-association region, part B can, for example, comprise different self-association regions, each specific for a different protein.

The interferer used for interference with the biological function of at least one target protein is not naturally present in nature and can be made through chemical synthesis or through recombinant protein expression or through a combination of the latter.

Thus, an interferor molecule comprises at least one self-association region (thus, part B comprises at least one self-association region). A "self-association region" is herein defined as a contiguous sequence of amino acids that has a high tendency to form a tight molecular assembly with identical or very closely related sequences. The wording "has a high tendency to form a tight molecular assembly" can also be construed as "has a high affinity." Affinity is usually translated into values of dissociation (Kd-values). Kd-values between interferor and target proteins are typically lying between micromolar and nanomolar ranges, but can be sub-nanomolar or supra-micromolar. Examples of self-association regions are intermolecular beta sheet regions, alpha-helical elements, hairpin loops, transmembrane sequences and signal sequences. In certain embodiments, at least one self-association region is present in part B. In certain embodiments, at least two self-association regions are present in part B. In certain embodiments, 3, 4, 5, 6 or more self-association regions are present in part B. The self-association regions can be interconnected by a linker region (e.g., a spacer of about two to about four amino acids). One (or at least one) self-association region present in part B is derived from a target protein. In certain embodiments, 2, 3, 4, 5, 6 or more self-association regions in part B are derived from a target protein. In certain embodiments, 2, 3, 4, 5, 6 or more self-association regions in part B are derived from more than one target protein. In certain embodiments, the at least two self-association regions present in part B are derived from the same target protein. The target protein is defined herein as the protein with which one wants to interfere with its function. Thus, in order to make part B specific for at least one protein, at least one self-association region in part B should be "derived from" the target protein or at least one self-association region should be present in the target protein. "Derived from" means that at least one contiguous self-associating region should be identical or homologous in amino acid sequence to a contiguous region of the target protein. In certain embodiments, the at least one self-associating region is at least 60%, at least 65%, at least 70%, at least 75%, at least 80%, at least 85%, at least 90%, at least 95% or at least 100% identical to the self-association region present in the target protein region.

Preferably, the length of a self-association region consists of at least three contiguous amino acids. In certain embodiments, the region consists of about three to about 30 amino acids. In certain embodiments, the region consists of about three to about 25 amino acids. In a particularly preferred embodiment, the region consists of about five to about 20 amino acids.

Self-association regions present in part B of the interferor molecule also can be determined and isolated from proteins other than the target protein and the self-association regions are coupled with at least one self-association region derived from the target protein, optionally with a spacer (or linker) between the self-association regions. For example, self-association regions that can be used can be derived from self-association regions of proteins that do not normally occur in the host in which the down-regulation of the biological function of a target protein is performed (thus some self-association regions in part B can be taken from an unrelated organism). The nature of the self-association regions determine the level of inhibition (id est the strength of inhibition) of a target protein through induced aggregation. More than one self-association region can be used from a target protein in an interferer molecule but also synthetic self-association regions or self-association regions derived from a different target protein can be used in combination with one or more self-association regions from a target protein.

In certain embodiments, such self-association regions consist of a synthetic sequence that is not derived from existing proteins and hence does not occur in nature. Examples of such synthetic self-association regions are described in M. López de la Paz et al. (2002), *PNAS* 99, 25, p. 16053, Table 1, which is herein incorporated by reference.

If at least one self-association region (id est the part B of the interferer molecule) has a hydrophobic character (because of its aggregation-inducing properties) it is preferably fused (or linked or coupled, which are equivalent terms) to a moiety (id est part A of the interferor molecule) that prevents aggregation of the self-association region and exposes the self-association region in direct contact with the solvent in which the interferer is present. As such, in certain embodiments, part A has a solubilizing function to keep part B in solution. In such embodiments, part A is, for example, a peptide, a protein domain, a protein (preferably different from the target protein, see Example 2), a glycosylation structure, a (hydrophilic) chemical group or a cyclodextrin or derivative thereof. In certain other embodiments, part A is an agarose bead, a latex bead, a cellulose bead, a magnetic bead, a silica bead, a polyacrylamide bead, a microsphere, a glass bead or any solid support (e.g., polystyrene, plastic, nitrocellulose membrane, glass).

In the interferer molecules, part B and part A may be optionally linked (or coupled) by means of a linker region (a spacer is an equivalent word). The linker region can, for instance, be an unnatural linker made by chemical synthesis (e.g., a flexible linker such as a hydroxy-substituted alkane chain, dextran, polyethylene glycol, or the linker can also consist of amino acid homologues) or the linker can exist of natural amino acids such as a poly(threonine) or poly(serine). Preferentially, when the linker comprises amino acids, the length of the linker region is between about three and about 15 amino acids, more preferably between about five and about ten amino acids. Often, a flexible linker can be chosen, but it is envisaged that a stiff linker will also work. Flexible linker sequences can be taken from nature, mostly such regions connect domains in naturally occurring proteins, such as the linker between the SH2 and SH3 domains src tyrosine kinase or the linker between the BRCT domains of BRCA 1.

The term "contacting" refers to the process in which the interferor and the target protein interact. In one form, the interferer is added (e.g., interferer is present at a particular concentration in a solution) to a sample comprising the target protein. In another form, the interferer molecule is injected into an organism comprising the target protein. Contacting can, for example, also be carried out through the process of transformation of a cell comprising the target protein, e.g., an isolated cell, e.g., in cell culture, a unicellular microorganism or a cell or a plurality of cells within a multicellular organism. Transformation implies that the interferor molecule is introduced in a host (e.g., a cell) through commonly known transfection or transformation methods (e.g., by gene transfer techniques including calcium phosphate, DEAE-dextran, electroporation, microinjection, viral methods, the use of cationic liposomes (see, for example, P. L. Feigner et al. (1987), *Proc. Natl. Acad. Sci. USA* 84:7413), commercially available cationic lipid formulations, e.g., Tfx 50 (Promega) or LIPOFECTAMIN2000™ (Life Technologies), particle bombardment, etc.). The interferer molecule may be encoded by a recombinant vector (e.g., a plasmid, cosmid, viral vector) and can be synthesized inside a host.

In an alternative embodiment, the interferer molecule can be introduced into a cell through carrier-mediated delivery, e.g., by liposomal carriers or nano-particles or by injection. In yet another alternative embodiment, the interferor molecule can enter a cell through a sequence that mediates cell penetration (or cell translocation). In the latter case, the interferer molecule is further modified through the recombinant or synthetic attachment of a cell penetration sequence. Thus, the interferor molecule (e.g., as a polypeptide) may be further fused or chemically coupled to a sequence facilitating transduction of the fusion or chemically coupled proteins into prokaryotic or eukaryotic cells. Sequences facilitating protein transduction are known to the person skilled in the art and include, but are not limited to, Protein Transduction Domains. Preferably, the sequence is selected from the group comprising the HIV TAT protein, a polyarginine sequence, penetratin and pep-1. Still other commonly used cell-permeable peptides (both natural and artificial peptides) are disclosed in A. Joliot and A. Prochiantz (2004) *Nature Cell Biol.* 6 (3) 189-193.

In certain embodiments, the interferor essentially consists of amino acids. In some embodiments, the sequences of parts A and B from the interferor molecule are derived from the same target protein. In other embodiments, the interferor is a chimeric molecule meaning that the sequences from parts A and B are derived from different proteins, e.g., part A is derived from one protein and at least one aggregation region of part B is derived from the target protein. A "polypeptide" refers to a polymer in which the monomers are amino acids and are joined together through amide bonds, alternatively referred to as a peptide. When the amino acids are alpha-amino acids, either the L-optical isomer or the D-optical isomer can be used. Additionally, unnatural amino acids, for example, beta-alanine, phenylglycine and homoarginine are also included. Commonly encountered amino acids that are not gene-encoded may also be used in the invention. All or part of the amino acids used in the interferors may be either the D- or L-isomer. In addition, other peptidomimetics are also useful in the invention. We specifically refer and incorporate herein the review of the development and use of peptidomimetics as antagonists for protein-protein interactions from L. O, Sillerud and R. S. Larson (2005), *Curr. Protein Pept. Sci.* 6(2):151-69.

Furthermore, D-amino acids can be added to the peptide sequence to stabilize turn features (especially in the case of glycine). In another approach, alpha, beta, gamma or delta turn mimics (such as alpha, beta, gamma, or delta di-peptides) can be employed to mimic structural motifs and turn features in a peptide and simultaneously provide stability from proteolysis and enhance other properties such as, for example, conformational stability and solubility.

Isolation of a Self-Association Region from a Target Protein

Self-association sequences are often hydrophobic, but this is not always the case. For example, the self-associating regions of the yeast prions are rather polar. In fact, cross-beta aggregation of an amino acid region derived from a polypeptide or protein can be initiated when (1) it has a high hydrophobicity, (2) it has a good β-sheet propensity, (3) it has a low net charge and (4) it is solvent-exposed. Thus, self-association protein regions ("segment" is an equivalent term for "region") are most often buried in the folded state and are not exposed to the solvent. The latter is confirmed by the experimental finding that in many globular proteins, aggregation occurs during refolding or under conditions in which denatured or partially folded states are significantly populated, i.e., at high concentration or as a result of destabilizing conditions or mutations.

Based on these findings, computer algorithms were developed that are able to predict self-association regions ("β-aggregating stretches or segments" is an equivalent wording) in proteins. One such algorithm, TANGO, is based on a statistical mechanics algorithm that considers the three physico-chemical parameters described above but also considers competition between different structural conformations: beta-turn, alpha-helix, beta-sheet aggregates and the folded state (A. M. Fernandez-Escamilla et al. (2004) *Nat. Biotechnol.* 22, 1302-1306, especially the Methods section on pages 1305 and 1306 are herein specifically incorporated by reference and also the Supplementary Notes 1 and 2 of the same article for further details on the methods and the data sets used for the calibration and the testing of the TANGO algorithm). Thus, self-association regions present in target proteins are obtainable by computer algorithms such as TANGO.

Self-association regions are often buried inside the core of target proteins,[10] effectively shielding the peptide from intermolecular association by an energy barrier corresponding to the stability of the target proteins.[11] In its normal environment (e.g., cytoplasm, extracellular matrix) the target protein has assistance from molecular chaperones that assist the protein in keeping its functional, monomeric form.[12] The model used by TANGO algorithm[6] is designed to predict beta-aggregation in peptides and proteins and consists of phase-space encompassing the random coil and the native conformations as well as other major conformational states, namely beta-turn, alpha-helix and beta aggregate. Every segment of a peptide can populate each of these states according to a Boltzmann distribution. Therefore, to predict self-association regions of a peptide, TANGO simply calculates the partition function of the phas-space. To estimate the aggregation tendency of a particular amino acid sequence, the following assumptions are made: (i) in ordered beta-sheet aggregate, the main secondary structure is the beta-strand; (ii) the regions involved in the aggregation process are fully buried, thus paying full solvation costs and gains, full entropy and optimizing their H-bond potential (that is, the number of H-bonds made in the aggregate is related to the number of donor groups that are compensated by acceptors; and excess of donors or acceptors remains unsatisfied); (iii) complementary charges in the selected window establish favorable electrostatic interactions, and overall net charge of the peptide insided, but also outside, the window disfavors aggregation. TANGO can be accessed on the World Wide Web at www.tango.emble.de.

The zyggregator algorithm is another example (A. P. Pawar et al. (2005), *J. Mol. Biol.* 350:379-392). These algorithms identify aggregation-prone sequences by comparing the aggregation propensity score of a given amino acid sequence with an average propensity calculated from a set of sequences of similar length.

In the invention, we estimate that a self-association region identified within a target protein with a TANGO score of 5% corresponds to an aggregation risk in vitro of 95%.[6] It was calculated that 85% of proteins from the human proteome that are not related to disease have at least one region with a TANGO score above the experimentally determined threshold of 5%. This shows that although more than 85% of the human proteins contain at least one single self-association region that aggregation is prevented because of the normal stability of the protein and the assistance from the chaperone machinery. The invention isolates these self-association regions from target proteins for the preparation of interferor molecules that are used for the specific induction of protein aggregation. The B-part of the interferer molecules comprises at least one aggregation region and at least one aggregation region is derived from a target protein. It is possible to control the strength of the protein interference (the strength of protein interference is, for example, the percentage of loss of biological function of a target protein when the protein or cell comprising the protein is contacted with a specific interferor molecule) through the incorporation of more than one aggregation region of a target protein in the B-part of the interferer molecule. Indeed, aggregation regions derived from a target protein with a low TANGO score (typically between 5% to about 20%) can be repeated in the B-part of the interferor to 2, 3, 4 or more aggregation regions. As an alternative embodiment, 1, 2 or 3 or 4 or more different aggregation regions with a low TANGO score derived from the same protein can be incorporated into the B-part of the interferor. As another alternative embodiment, 1, 2, 3, 4 or more synthetic aggregation regions (thus, not derived from the target protein) can be combined with 1, 2, 3, 4, or more aggregation regions derived from the target protein into the B-part to enhance the down-regulation of a target protein with a low TANGO score.

Thus, in certain embodiment, provided are non-naturally occurring molecules capable of aggregating a target protein. In certain embodiments, the non-naturally molecule is proteinaceous in nature. "Proteinaceous" means that the molecule comprises L-amino acids or D-amino acids or a mixture of L- and D-amino acids or a combination of natural amino acids and peptidomimetics.

In certain embodiments, provided are non-naturally occurring molecules comprising at least one self-association region isolated from a protein domain capable of being soluble in water, wherein the self-association region is fused to a moiety that prevents aggregation of the self-association region.

In certain embodiments, provided are non-naturally occurring molecules comprising at least one self-association region isolated from a protein domain capable of being soluble in water, wherein the self-association region is fused to a moiety that prevents aggregation of the self-association region so that the self-association region is in direct contact with the solvent wherein it is present.

In certain embodiments, provided are non-naturally occurring molecules consisting of at least one self-association region isolated from a protein domain capable of being soluble in water, wherein the self-association region is fused to a moiety that prevents aggregation of the self-association region.

In certain embodiments, provided are non-naturally occurring molecules consisting of at least one self-association region isolated from a protein domain capable of being soluble in water, wherein the self-association region is fused to a moiety that prevents aggregation of the self-association region so that the self-association region is in direct contact with the solvent wherein it is present.

In certain embodiments, such a moiety is, for example, a peptide, an agarose bead, a protein domain or a protein. In certain embodiments, the non-naturally occurring molecule comprises at least two self-association regions of which at least one self-association region is derived from a target protein.

In other words, provided are non-naturally occurring molecules, which comprise part A and part B, wherein i) part A comprises a region, such as a peptide, protein domain, protein or agarose bead preventing the aggregation of part B, and ii) part B, which comprise at least one self-association region, wherein the region consists of at least three contiguous amino acids, and wherein the region is isolated from the protein, which function is to be interfered with, and wherein a linker is optionally present between parts A and B.

In still other words, provided are non-naturally occurring molecules, which comprise part A and part B, wherein i) part A comprises a region, such as a peptide, protein domain or agarose bead preventing the aggregation of part B, and ii) part B, which comprises at least one self-association region consisting of at least three contiguous amino acids, and wherein at least one self-association region is isolated from a protein, which function is to be interfered with, and wherein the region is isolated from a domain from the protein, which is capable of being soluble in water, and wherein a linker is optionally present between parts A and B, and wherein part B is in direct contact to the environment wherein the molecule and the protein are present.

In still other words, provided is a non-naturally occurring molecule, which comprises part A and part B, wherein i) part A comprises a region, such as a peptide, protein domain or agarose bead preventing the aggregation of part B, and ii) part B, which consists of at least one self-association region consisting of at least three contiguous amino acids and wherein, the at least one self-association region is isolated from a protein, which function is to be interfered with, and wherein the region is derived from a domain from the protein, which is capable of being soluble in water, and wherein a linker is optionally present between parts A and B, and wherein part B is in direct contact to the environment wherein the molecule and the protein are present.

The wording "isolated (or derived form) from a domain from the protein, which is capable of being soluble in water" means that a self-association region is a contiguous amino acid sequence isolated from a soluble domain of a protein. The latter also means that self-association regions derived from transmembrane regions or self-association regions derived from signal sequences are specifically excluded in the claim scope of these interferor molecule products in such embodiments.

The at least one self-association region of the interferor molecule (id est part B of the interferor molecule) is "in direct contact" with the environment (e.g., solvent, cytosol) in which the interferor molecule is present. The importance of this is clarified further. In globular proteins, self-association sequences (also designated as "aggregation nucleating regions") are generally buried in the hydrophobic core of the globular protein and, as such, kept protected from the solvent by a dense network of cooperative interactions stabilizing the native state. Hence, under normal circumstances, there is no "direct contact" between the self-association region and the environment (for example, the solvent). Only when the protein is unfolded, for example, when it is synthesized on the ribosome or destabilized by mutation, change of temperature, pH or loss of a specific chaperone, thereby favoring the unfolded state, will it expose its self-association regions to the environment. Self-association regions are normally buried inside proteins (in order to prevent aggregation) and in the non-natural interferor molecule, the self-association regions have been isolated and exposed to the environment by linking the regions to a moiety that prevents aggregation (id est part A of the interferor molecule). In still other words, the non-naturally interferer molecule does not fold into a globular structure and, therefore, the at least one self-association region (id est part B) in the non-natural interferor molecule is in direct contact with the solvent in which the interferer molecule is present. Hence, "in direct contact" refers to the opposite of "being buried and kept protected from."

In certain embodiments, the interferer molecules that comprise at least one self-association region derived from a soluble protein domain are polypeptides.

In certain embodiments, provided is a recombinant vector comprising a polynucleotide encoding such interferor molecules.

In certain embodiments, the interferor molecules are used as a medicament.

Therapeutic Applications of the Interferer Molecules

Proteins are responsible for biological activities ranging from numerous enzymatic reactions, over-transduction of signals to providing structure. Changes in protein structure, abundance or activity are at the root cause of many diseases. Many drugs act via specific interference with one or a limited number of proteins. Provided are methods to develop a novel class of compounds able to specifically interfere with a target protein of choice. These novel compounds are designated as "interferors".

Thus, in certain embodiments, provided is the use as a medicament of a non-naturally occurring molecule, the molecule comprising at least one self-association region derived from a protein domain capable of being soluble in water, wherein the self-association region is fused to a moiety that prevents aggregation of the self-association region.

In certain embodiments, provided is the use as a medicament of a non-naturally occurring molecule comprising at least one self-association region derived from a protein domain capable of being soluble in water, wherein the self-association region is fused to a moiety that prevents aggregation of the self-association region so that the self-association region is in direct contact with the solvent wherein the molecule is present.

In still other words, provided is the use as a medicament of a non-naturally occurring interferor molecule, which comprises part A and part B, wherein i) part A comprises a region, such as a peptide or protein domain preventing the aggregation of part B, and ii) part B comprises at least one self-association region, wherein the region comprises at least three contiguous amino acids derived from the target protein, and wherein a linker is optionally present between parts A and B.

In still other words, provided is the use as a medicament of a non-naturally occurring interferer molecule, which comprises part A and part B, wherein i) part A comprises a region, such as a peptide or protein domain preventing the aggregation of part B, and ii) part B comprises at least one self-association region, wherein the region comprises at least three contiguous amino acids derived from the target protein, and wherein a linker is optionally present between parts A and B, and wherein part B is in direct contact with the solvent wherein the interferor molecule is present.

The interferor molecules can be used for treating diseases and/or in the manufacturing of a medicament to treat diseases, such as cancer, associated with the aberrant expression of at least one target protein, such as an oncogenic protein. The term "aberrant expression" refers to, for example, the (over) expression of an oncogenic protein in the case of cancer. It also includes the expression of a dominant negative protein, the undesired localization of a particular protein or splice variant of a particular protein, the undesired expression of a particular splice variant of a particular protein, the higher activity of a mutant protein or the higher activity of a particular protein.

In certain embodiments, the "aberrant expression" refers to the unwanted presence of a post-translationally modified protein or to the undesired presence of a non-post-translationally modified protein. Post-translational modifications alter the physico-chemical properties of the modified amino acids and, as such, they have the potential of altering the aggregation tendency of a given polypeptide segment that can be exploited to specifically target the form that has the strongest aggregation tendency. So if a post-translational modification significantly decreases the aggregation tendency of the self-association region, then interference will be most efficient with the unmodified protein. In contrast, in case of post-translational modifications that increase the aggregation tendency of the self-association region, then interference will be most efficient with the modified protein. Based on the hydrophobicity alone, it is assumed that modifications such as phosphorylation and glycosylation will decrease aggregation tendency, whereas lipid attachment will increase aggregation tendency.

The target protein to which the interferer molecule of the invention is directed may be associated with a pathological condition. For example, the protein may be a pathogen-associated protein, e.g., a viral protein, a tumor-associated protein, or an autoimmune disease-associated protein. In one aspect, the invention features a method of treating a subject at risk for or afflicted with unwanted cell proliferation, e.g., malignant or non-malignant cell proliferation. The method includes: providing an interferor molecule, e.g., an interferor having a structure as described herein, wherein the interferer molecule is capable of interfering with (inhibiting) the function and/or presence of a protein that promoted unwanted cell proliferation and administering the interferor to a subject, preferably a human subject, thereby treating the subject.

In certain embodiments, the protein is a growth factor or growth factor receptor, a kinase (e.g., a protein tyrosine, serine or threonine kinase), an adaptor protein, a protein from the G protein-coupled receptor super-family, or a transcription factor.

In certain embodiments, the interferer molecule interferes with the biological function of the PDGF-beta protein and, thus, can be used to treat a subject having or at risk for a disorder characterized by unwanted PDGF-beta expression, e.g., testicular and lung cancers.

In certain embodiments, the interferer inhibits (knocks down) the function and/or presence of the Erb-B protein and, thus, can be used to treat a subject having or at risk for a disorder characterized by unwanted Erb-B expression, e.g., breast cancer.

In certain embodiments, the interferor inhibits the function (or "interferes with the function," which is equivalent) of (or interferes with the presence of) the Src protein and, thus, can be used to treat a subject having or at risk for a disorder characterized by unwanted Src expression, e.g., colon cancers.

In certain embodiments, the interferor inhibits the function and/or presence of the CRK protein and, thus, can be used to treat a subject having or at risk for a disorder characterized by unwanted CRK expression, e.g., colon and lung cancers.

In certain embodiments, the interferor interferes with the function and/or presence of the GRB2 protein and, thus, can be used to treat a subject having or at risk for a disorder characterized by unwanted GRB2 expression, e.g., squamous cell carcinoma.

In certain embodiments, the interferor molecule interferes with the function and/or presence of the RAS gene and, thus, can be used to treat a subject having or at risk for a disorder characterized by unwanted RAS expression, e.g., pancreatic, colon and lung cancers, and chronic leukemia.

In certain embodiments, the interferor molecule interferes with the function and/or presence of the MEKK protein and, thus, can be used to treat a subject having or at risk for a disorder characterized by unwanted MEKK expression, e.g., squamous cell carcinoma, melanoma or leukemia.

In certain embodiments, the interferor molecule interferes with the function and/or presence of the JNK protein and, thus, can be used to treat a subject having or at risk for a disorder characterized by unwanted JNK expression, e.g., pancreatic or breast cancers.

In certain embodiments, the interferor molecule interferes with the function and/or presence of the RAF protein and, thus, can be used to treat a subject having or at risk for a disorder characterized by unwanted RAP expression, e.g., lung cancer or leukemia.

In certain embodiments, the interferer molecule interferes with the function and/or presence of the Erk1/2 protein and, thus, can be used to treat a subject having or at risk for a disorder characterized by unwanted Erk1/2 expression, e.g., lung cancer.

In certain embodiments, the interferor molecule interferes with the function and/or presence of the PCNA (p21) protein and, thus, can be used to treat a subject having or at risk for a disorder characterized by unwanted PCNA expression, e.g., lung cancer.

In certain embodiments, the interferor molecule interferes with the function and/or presence of the MYB protein and, thus, can be used to treat a subject having or at risk for a disorder characterized by unwanted MYB expression, e.g., colon cancer or chronic myelogenous leukemia.

In certain embodiments, the interferor molecule interferes with the function and/or presence of the c-MYC protein and, thus, can be used to treat a subject having or at risk for a disorder characterized by unwanted c-MYC expression, e.g., Burkitt's lymphoma or neuroblastoma.

In certain embodiments, the interferor molecule interferes with the function and/or presence of the JUN protein and, thus, can be used to treat a subject having or at risk for a disorder characterized by unwanted JUN expression, e.g., ovarian, prostate or breast cancers.

In certain embodiments, the interferer molecule interferes with the function and/or presence of the FOS protein and, thus, can be used to treat a subject having or at risk for a disorder characterized by unwanted FOS expression, e.g., skin or prostate cancers.

In certain embodiments, the interferor molecule inhibits the function and/or presence of the BCL-2 protein and, thus, can be used to treat a subject having or at risk for a disorder characterized by unwanted BCL-2 expression, e.g., lung or prostate cancers or non-Hodgkin lymphoma.

In certain embodiments, the interferer molecule interferes with the function and/or presence of the Cyclin D protein, and thus can be used to treat a subject having or at risk for a disorder characterized by unwanted Cyclin D expression, e.g., esophageal and colon cancers.

In certain embodiments, the interferor molecule interferes with the function and/or presence of the VEGF protein and, thus, can be used to treat a subject having or at risk for a disorder characterized by unwanted VEGF expression, e.g., esophageal, colon cancers or pathological angiogenesis.

In certain embodiments, the interferor molecule interferes with the function and/or presence of the EGFR protein and, thus, can be used to treat a subject having or at risk for a disorder characterized by unwanted EGFR expression, e.g., breast cancer.

In certain embodiments, the interferer molecule interferes with the function and/or presence of the Cyclin A protein and, thus, can be used to treat a subject having or at risk for a disorder characterized by unwanted Cyclin A expression, e.g., lung and cervical cancers.

In certain embodiments, the interferer molecule interferes with the function and/or presence of the Cyclin E protein and, thus, can be used to treat a subject having or at risk for a disorder characterized by unwanted Cyclin E expression, e.g., lung and breast cancers.

In certain embodiments, the interferer molecule interferes with the function and/or presence of the WNT-1 protein and, thus, can be used to treat a subject having or at risk for a disorder characterized by unwanted WNT-1 expression, e.g., basal cell carcinoma.

In certain embodiments, the interferer molecule interferes with the function and/or presence of the beta-catenin protein and, thus, can be used to treat a subject having or at risk for a disorder characterized by unwanted beta-catenin expression, e.g., adenocarcinoma or hepatocellular carcinoma.

In certain embodiments, the interferer molecule interferes with the function and/or presence of the c-MET protein and, thus, can be used to treat a subject having or at risk for a disorder characterized by unwanted c-MET expression, e.g., hepatocellular carcinoma.

In certain embodiments, the interferer molecule interferes with the function and/or presence of the protein kinase C (PKC) protein and, thus, can be used to treat a subject having or at risk for a disorder characterized by unwanted PKC expression, e.g., breast cancer.

In certain embodiments, the interferor molecule interferes with the function and/or presence of the NFKappa-B protein and, thus, can be used to treat a subject having or at risk for a disorder characterized by unwanted NFKappa-B expression, e.g., breast cancer.

In certain embodiments, the interferer molecule interferes with the function and/or presence of the STAT3 protein and, thus, can be used to treat a subject having or at risk for a disorder characterized by unwanted STAT3 expression, e.g., prostate cancer.

In certain embodiments, the interferer molecule interferes with the function and/or presence of the survivin protein and, thus, can be used to treat a subject having or at risk for a disorder characterized by unwanted survivin expression, e.g., cervical or pancreatic cancers.

In certain embodiments, the interferor molecule interferes with the function and/or presence of the Her2/Neu protein and, thus, can be used to treat a subject having or at risk for a disorder characterized by unwanted Her2/Neu expression, e.g., breast cancer.

In certain embodiments, the interferor molecule interferes with the function and/or presence of the topoisomerase I protein and, thus, can be used to treat a subject having or at risk for a disorder characterized by unwanted topoisomerase I expression, e.g., ovarian and colon cancers.

In certain embodiments, the interferor molecule interferes with the function and/or presence of the topoisomerase II alpha protein and, thus, can be used to treat a subject having or at risk for a disorder characterized by unwanted topoisomerase II expression, e.g., breast and colon cancers.

In another aspect, provided is a method of treating a subject, e.g., a human, at risk for or afflicted with a disease or disorder that may benefit from angiogenesis inhibition, e.g., cancer. The method includes: providing an interferor molecule, e.g., an interferor molecule having a structure described herein, which interferor molecule can inhibit (or interfere with the function) a protein that mediates angiogenesis and administering the interferor molecule to a subject, thereby treating the subject.

In certain embodiments, the interferor molecule interferes with the function and/or presence of the alpha v-integrin protein and, thus, can be used to treat a subject having or at risk for a disorder characterized by unwanted alpha v-integrin, e.g., brain tumors or tumors of epithelial origin.

In certain embodiments, the interferor molecule interferes with the function and/or presence of the Flt-1 receptor protein and, thus, can be used to treat a subject having or at risk for a disorder characterized by unwanted Flt-1 receptors, e.g., cancer and rheumatoid arthritis.

In certain embodiments, the interferor molecule interferes with the function and/or presence of the tubulin protein and, thus, can be used to treat a subject having or at risk for a disorder characterized by unwanted tubulin, e.g., cancer and retinal neovascularization.

In another aspect, provided is a method of treating a subject infected with a virus or at risk for or afflicted with a disorder or disease associated with a viral infection. The method includes: providing an interferor molecule, e.g., an interferor molecule having a structure described herein, which interferer molecule is homologous to and can silence a viral protein or a cellular protein, which mediates viral function, e.g., entry or growth; and administering the interferor molecule to a subject, preferably a human subject, thereby treating the subject. As such, provided is methods of using interferors for the manufacture of a medicament to treat patients infected by viruses including the Human Papilloma Virus, Human Immunodeficiency Virus (HIV), Hepatitis B Virus (HBV), Hepatitis A Virus (HAV), Hepatitis C Virus (HCV), Respiratory Syncytial Virus (RSV), Herpes Simplex Virus (HSV), Cytomegalovirus (CMV), Epstein Barr-Virus (EBV), a rhinovirus, West Nile Virus, Tick-borne encephalitis virus, measles virus (MV), or poliovirus.

In another aspect, the invention features methods of treating a subject infected with a pathogen, e.g., a bacterial, amoebic, parasitic, or fungal pathogen. The method includes: providing an interferor molecule, e.g., an interferer molecule having a structure described herein, wherein the interferer molecule is capable of interfering with the function of a pathogenic protein derived from the pathogen and administering the interferor molecule to a subject, preferably a human subject, thereby treating the subject. The target protein from the pathogen can be one involved in growth, cell wall synthesis, protein synthesis, transcription, energy metabolism (e.g., the Krebs cycle) or toxin production. Thus, provided is for a method of treating patients infected by, for example, *Plasmodium falciparum, Mycobacterium ulcerans, Mycobacterium tuberculosis, Mycobacterium leprae, Staphylococcus aureus, Streptococcus pneumoniae, Streptococcus pyogenes, Chlamydia pneumoniae*, or *Mycoplasma pneumoniae*.

In another aspect, provided is a method of treating a subject, e.g., a human, at risk for or afflicted with a disease or disorder characterized by an unwanted immune response, e.g., an inflammatory disease or disorder, or an autoimmune disease or disorder. The method includes: providing an interferer molecule, e.g., an interferor molecule having a structure described herein, which interferor molecule is capable of inhibiting (down-regulating) the function and/or presence of a protein, which mediates an unwanted immune response, and administering the interferor molecule to a subject, thereby treating the subject.

In certain embodiments, the disease or disorder is an ischemia or reperfusion injury, e.g., ischemia or reperfusion injury associated with acute myocardial infarction, unstable angina, cardiopulmonary bypass, surgical intervention (e.g., angioplasty, such as percutaneous transluminal coronary angioplasty), a response to a transplanted organ or tissue (e.g., transplanted cardiac or vascular tissue), or thrombolysis.

In certain embodiments, the disease or disorder is restenosis, e.g., restenosis associated with surgical intervention (e.g., angioplasty, such as percutaneous transluminal coronary angioplasty).

In certain embodiments, the disease or disorder is Inflammatory Bowel Disease, e.g., Crohn's Disease or Ulcerative Colitis. In certain embodiments, the disease or disorder is inflammation associated with an infection or injury. In certain embodiments, the disease or disorder is asthma, lupus, multiple sclerosis, diabetes, e.g., type II diabetes, arthritis, e.g., rheumatoid or psoriatic.

In certain embodiments, the interferor molecule interferes with the function of an integrin or co-ligand thereof, e.g., VLA4, VCAM, ICAM. In certain embodiments, the interferor molecule interferes with the function of a selectin or co-ligand thereof, e.g., P-selectin, E-selectin (ELAM), L-selectin, or P-selectin glycoprotein-(PSGLI). In certain embodiments, the interferor molecule interferes with the function of a component of the complement system, e.g., C3, C5, C3aR, C5aR, C3 convertase, C5 convertase. In certain embodiments, the interferor molecule interferes with the function of a chemokine or receptor thereof, e.g., TNF-α, IL-1α, IL-1, IL-2, IL-2R, IL-4, IL-4R, IL-5, IL-6, IL-8, TNFRI, TNFRII, IgE, SCYA11 or CCR3.

In another aspect, provided is a method of treating a subject, e.g., a human, at risk for or afflicted with acute pain or chronic pain. The method includes providing an interferor molecule, e.g., an interferor molecule having a structure described herein, which interferor molecule is capable of interfering with a protein, which mediates the processing of pain and administering the interferor molecule to a subject, thereby treating the subject. In certain embodiments, the interferor molecule interferes with the function of a component of an ion channel. In another particularly preferred embodiment, the interferor molecule interferes with the function of a neurotransmitter receptor or ligand.

In another aspect, the invention features a method of treating a subject, e.g., a human, at risk for or afflicted with a neurological disease or disorder. The method includes providing an interferor molecule, e.g., an interferor molecule having a structure described herein, which interferor molecule is capable of interfering with a protein, which mediates a neurological disease or disorder and administering the interferor molecule to a subject, thereby treating the subject. In particular embodiments, the diseases (or disorders) that can be treated include Alzheimer's Disease (in this case, the interferer molecule interferes with the function of a secretase, which leads to the processing of APP, e.g., a protein involved in the gamma-secretase complex, e.g., presenilin protein 1 or 2, an Aph1 protein, nicastrin, BACE1 or BACE2). The interferer inhibits the processing of APP and prevents the formation of insoluble amyloid beta. The same strategy can be used to prevent and/or to treat other neurodegenerative diseases, such as Huntington's disease, a spinocerebellar ataxia (e.g., SCA1, SCA2, SCA3 (Machado-Joseph disease), SCA7 or SCA8).

Thus, in one aspect, provided is a method for the production or manufacture of a medicament or a pharmaceutical composition comprising at least one interferer molecule and furthermore mixing the interferor molecule with a pharmaceutically acceptable carrier. In certain embodiments, the interferor molecule is a polypeptide and can be made synthetically or as a recombinant protein. The recombinant protein may be manufactured using recombinant expression systems comprising bacterial cells, yeast cells, animal cells, insect cells, plant cells or transgenic animals or plants. The recombinant protein may be purified by any conventional protein purification procedure close to homogeneity and/or be mixed with additives.

The administration of a pharmaceutical composition comprising an interferer molecule may be by way of oral, inhaled, transdermal or parenteral (including intravenous, intratumoral, intraperitoneal, intramuscular, intracavity, and subcutaneous) administration. The active compound may be administered alone or preferably formulated as a pharmaceutical composition. A unit dose will normally contain 0.01 to 500 mg, for example 0.01 to 50 mg, or 0.01 to 10 mg, or 0.05 to 2 mg of compound or a pharmaceutically acceptable salt thereof. Unit doses will normally be administered once or more than once a day, for example, two, three, or four times a day, more usually one to three times a day, such that the total daily dose is normally in the range of 0.0001 to 10 mg/kg; thus, a suitable total daily dose for a 70 kg adult is 0.01 to 700 mg, for example, 0.01 to 100 mg, or 0.01 to 10 mg or more, usually 0.05 to 10 mg.

It is preferred that the compound or a pharmaceutically acceptable salt thereof is administered in the form of a unit-dose composition, such as a unit dose oral, parenteral, transdermal or inhaled composition. Such compositions are prepared by admixture and are suitably adapted for oral, inhaled, transdermal or parenteral administration and, as such, may be in the form of tablets, capsules, oral liquid preparations, powders, granules, lozenges, reconstitutable powders, injectable and infusable solutions or suspensions or suppositories or aerosols.

Tablets and capsules for oral administration are usually presented in a unit dose and contain conventional excipients such as binding agents, fillers, diluents, tabletting agents, lubricants, disintegrants, colorants, flavorings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycolate. Suitable lubricants include, for example, magnesium stearate. Suitable pharmaceutically acceptable wetting agents include sodium lauryl sulphate. These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example, sorbitol, syrup, methyl cellulose, gelatin, hydroxyethylcellulose, carboxymethyl cellulose, aluminum stearate gel or hydrogenated edible fats, emulsifying agents, for example, lecithin, sorbitan monooleate, or acacia; non-aqueous vehicles, which may include edible oils, for example, almond oil, fractionated coconut oil, oily esters such as esters of glycerine, propylene glycol, or ethyl alcohol; preservatives, for example, methyl or propyl p-hydroxybenzoate or sorbic acid and, if desired, conventional flavoring or coloring agents. Oral formulations also include conventional sustained release formulations, such as tablets or granules having an enteric coating.

Preferably, compositions for inhalation are presented for administration to the respiratory tract as a snuff or an aerosol or solution for a nebulizer, or as a microfine powder for insufflation, alone or in combination with an inert carrier such as lactose. In such a case, the particles of active compounds suitably have diameters of less than 50 microns, preferably less than 10 microns, for example, between 1 and 5 microns, such as between 2 and 5 microns. Alternatively, coated nanoparticles can be used with a particle size between 30 and 500 nm. A favored inhaled dose will be in the range of 0.05 to 2 mg, for example, 0.05 to 0.5 mg, 0.1 to 1 mg or 0.5 to 2 mg.

For parenteral administration, fluid unit dose forms are prepared containing a compound of the invention and a sterile vehicle. The active compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anesthetic, preservatives and buffering agents are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the active compound. Where appropriate, small amounts of bronchodilators, for example, sympathomimetic amines such as isoprenaline, isoetharine, salbutamol, phenylephrine and ephedrine; xanthine derivatives such as theophylline and aminophylline; corticosteroids such as prednisolone; and adrenal stimulants such as ACTH, may be included.

As is common practice, the compositions will usually be accompanied by written or printed directions for use in the medical treatment concerned.

In certain embodiments, the interferor molecule further comprises a protein transduction domain. It has been shown that a series of small protein domains, termed protein transduction domains (PTDs), cross biological membranes efficiently and independently of transporters or specific receptors and promote the delivery of peptides and proteins into cells. For example, the TAT protein from human immunodeficiency virus (HIV-1) is able to deliver biologically active proteins in vivo. Similarly, the third alpha-helix of Antennapedia homeodomain and VP22 protein from herpes simplex virus promote the delivery of covalently linked peptides or proteins into cells (reviewed in K. G. Ford et al. (2001), *Gene Ther.* 8:1-4). Protein delivery based on a short amphipathic peptide carrier, Pep-1, is efficient for delivery of a variety of peptides and proteins into several cell lines in a fully biologically active form, without the need for prior chemical covalent coupling (M. C. Morris et al. (2001), *Nat. Biotechnol.* 19:1173-1176). The capacity of VP22 chimeric proteins to spread from the primary transduced cell to surrounding cells can improve gene therapy approaches (L. Zender et al. (2002), *Cancer Gene Ther.* 9:489-496). Sequences facilitating protein transduction are known to the person skilled in the art and include, but are not limited to, Protein Transduction Domains. Preferably, the sequence is selected from the group comprising the HIV TAT protein, a polyarginine sequence, penetratin and pep-1. Still, other commonly used cell-permeable peptides (both natural and artificial peptides) are disclosed in A. Joliot and A. Prochiantz (2004), *Nature Cell Biol.* 6 (3) 189-193.

A second aspect of a pharmaceutical composition is the use of a nucleotide sequence encoding the interferer molecules. In the case where a nucleic acid sequence encoding the interferer molecule is used in a gene therapy treatment, the medicament is preferably intended for delivery of the nucleic acid into the cell. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386, 4,946,787, and 4,897,355, the contents of each of which are incorporated herein by this reference, and lipofection reagents are sold commercially (e.g., Transfectam™ and Lipofectin™). Cationic and neutral lipids that are suitable for efficient receptor-recognition lipofection of polynucleotides include those of Flegner, WO 91/17424, WO 91/16024. Delivery can be to cells (ex vivo administration) or target tissues (in vivo administration). The preparation of lipid: nucleic acid complexes, including targeted liposomes such as immunolipid complexes, is well known to one of skill in the art (see, e.g., Crystal, 1995; Blaese et al., 1995; *Behr*, 1994; Remy et al., 1994; Gao and Huang, 1995; U.S. Pat. Nos. 4,186,183, 4,217,344, 4,235,871, 4,261,975, 4,485,054, 4,501,728, 4,774,085, 4,837,028, and 4,946,787, the contents of each of which are incorporated herein by this reference).

The use of RNA or DNA viral-based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral-based systems for the delivery of nucleic acids include, amongst others, retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long-term expression of the inserted transgene.

Additionally, high transduction efficiencies have been observed in many different cell types and target tissues. In cases where transient expression of the nucleic acid is preferred, adenoviral-based systems, including replication-deficient adenoviral vectors, may be used. Adenoviral-based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors, including recombinant adeno-associated virus vectors, are also used to transduce cells with target nucleic acids, e.g., in the in vitro production of nucleic acids and peptides and for in vivo and ex vivo gene therapy procedures (see, e.g., U.S. Pat. No. 4,797,368; WO 93/24641; Kotin, 1994; the construction of recombinant AAV vectors is described in a number of publications, including U.S. Pat. No. 5,173,414; Hermonat and Muzyczka, 1984; Samulski et al., 1989, the contents of each of which are incorporated herein by this reference).

Gene therapy vectors can be delivered in vivo by administration to an individual patient, typically by systemic administration (e.g., intravenous, intraperitoneal, intramuscular, intratracheal, subdermal, or intracranial infusion) or topical application. In certain embodiments, the invention also envisages the use of a hydrodynamic gene therapeutic method. Hydrodynamic gene therapy is disclosed in U.S. Pat. No. 6,627,616 (Mirus Corporation, Madison), the contents of which are incorporated herein by this reference, and involves the intravascular delivery of non-viral nucleic acids encoding an interferor whereby the permeability of vessels is increased through, for example, the application of an increased pressure inside the vessel or through the co-administration of vessel permeability-increasing compounds such as, for example, papaverine.

Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells that have incorporated the vector. Ex vivo cell transfection for diagnostics, research, or for gene therapy (e.g., via re-infusion of the transfected cells into the host organism) is well known to those of skill in the art. In certain embodiments, cells are isolated from the subject organism, transfected with a nucleic acid (gene or cDNA), and re-infused back into the subject organism (e.g., patient). Various cell types suitable for ex vivo transfection are well known to those of skill in the art (see, e.g., Freshney et al., 1994, and the references cited therein for a discussion of how to isolate and culture cells from patients).

In certain embodiments, the method of protein interference of the invention may be used for determining the function of a protein in a cell or an organism being capable of mediating protein interference. The cell can be a prokaryotic cell or can be a eukaryotic cell or can be a cell line, e.g., a plant cell or an animal cell, such as a mammalian cell, e.g., an embryonic cell, a pluripotent stem cell, a tumor cell, e.g., a teratocarcinoma cell or a virus-infected cell. The organism is preferably a eukaryotic organism, e.g., a plant or an animal, such as a mammal, particularly a human.

The target protein to which the interferor molecule of the invention is directed may be associated with a pathological condition. For example, the protein may be a pathogen-associated protein, e.g., a viral protein, a tumor-associated protein or an autoimmune disease-associated protein. The target protein may also be a heterologous gene expressed in a recombinant cell or a genetically altered organism. By inhibiting the function of such a protein, valuable information and therapeutic benefits in the agricultural field or in the medicine or veterinary medicine field may be obtained. In a particularly preferred embodiment, the method of the invention is used with a eukaryotic cell or a eukaryotic non-human organism exhibiting a target protein-specific knockout phenotype comprising an at least partially deficient expression of at least one endogenous target protein, wherein the cell or organism is contacted with at least one interferor molecule capable of inhibiting the function of at least one endogenous target protein or with a vector encoding at least one interferor molecule capable of interfering with the function and/or presence of at least one endogenous protein. It should be noted that the invention also allows a target-specific knockout of several different endogenous proteins due to the specificity of the interferor molecule.

Protein-specific knockout phenotypes of cells or non-human organisms, particularly of human cells or non-human mammals, may be used in analytical procedures, e.g., in the functional and/or phenotypical analysis of complex physiological processes such as analysis of proteomes. For example, one may prepare the knock-out phenotypes of human proteins in cultured cells, which are assumed to be regulators of alternative splicing processes. Among these proteins are particularly the members of the SR splicing factor family, e.g., ASF/SF2, SC35, SRp20, SRp40 or SRp55. Further, the effect of SR proteins on the mRNA profiles of predetermined alternatively spliced genes such as CD44 may be analyzed.

Using the protein-based knockout technologies described herein, the expression of an endogenous target protein may be inhibited in a target cell or a target organism. The endogenous protein may be complemented by an exogenous target nucleic acid coding for the target protein or a variant or mutated form of the target protein, e.g., a gene or a cDNA, which may optionally be fused to a further nucleic acid sequence encoding a detectable peptide or polypeptide, e.g., an affinity tag, particularly a multiple affinity tag. Variants or mutated forms of the target protein differ from the endogenous target protein in that they differ from the endogenous protein by amino acid substitutions, insertions and/or deletions of single or multiple amino acids. The variants or mutated forms may have the same biological activity as the endogenous target protein. On the other hand, the variant or mutated target protein may also have a biological activity, which differs from the biological activity of the endogenous target protein, e.g., a partially deleted activity, a completely deleted activity, an enhanced activity, etc.

The complementation may be accomplished by co-expressing the polypeptide encoded by the exogenous nucleic acid, e.g., a fusion protein comprising the target protein and the affinity tag and the interferor molecule for knocking out the endogenous protein in the target cell. This co-expression may be accomplished by using a suitable expression vector expressing both the polypeptide encoded by the exogenous nucleic acid, e.g., the tag-modified target protein and the interferor molecule or alternatively by using a combination of expression vectors or alternatively the interferor molecule may contact the target cell from the outside of the cell. Proteins and protein complexes that are synthesized de novo in the target cell will contain the exogenous protein, e.g., the modified fusion protein.

In order to avoid suppression of the exogenous protein function with the interferor molecule, the exogenous protein must have sufficient amino acid differences in the aggregation region that is selected for the design of the interferor molecule. Alternatively, the endogenous target protein may be complemented by corresponding proteins from other species or the endogenous target protein may be complemented by a splice form of the target protein. The combination of knockout of an endogenous protein and rescue by using mutated, e.g., partially deleted exogenous target, has advantages compared to the use of a knockout cell. Further, this method is particularly suitable for identifying functional domains of the target protein.

In a further preferred embodiment, a comparison, e.g., of gene expression profiles and/or proteomes and/or phenotypic characteristics of at least two cells or organisms is carried out. These organisms are selected from: (i) a control cell or control organism without target protein inhibition, (ii) a cell or organism with target protein inhibition, and (iii) a cell or organism with target protein inhibition plus target protein complementation by an exogenous target nucleic acid encoding the target protein.

The described methods are also suitable in a procedure for identifying and/or characterizing pharmacological agents, e.g., identifying new pharmacological agents from a collection of test substances and/or characterizing mechanisms of action and/or side effects of known pharmacological agents. Thus, the invention also relates to a system for identifying and/or characterizing pharmacological agents acting on at least one target protein comprising: (a) a eukaryotic cell or a eukaryotic non-human organism capable of expressing at least one endogenous target gene coding for the target protein, (b) at least one interferer molecule capable of inhibiting the expression of the at least one endogenous target gene, and (c) a test substance or a collection of test substances, wherein pharmacological properties of the test substance or the collection are to be identified and/or characterized. Further, the system as described above preferably comprises: (d) at least one exogenous target nucleic acid coding for the target protein or a variant or mutated form or splice form of the target protein, wherein the exogenous target protein differs from the endogenous target protein on the amino acid level of the aggregation regions, such that the function of the exogenous target protein is substantially less inhibited by the interferer molecule than the expression of the endogenous protein.

In addition, the invention also includes cells and organisms comprising an interferor molecule. An organism can, for example, be a transgenic plant that carries the genetic information that encodes an interferor. Such a transgenic plant is in a preferred embodiment a silenced plant (id est in which a particular target protein is down-regulated because of the presence of a specific interferor in a sub-set of cells or organs or present in all cells and organs of the plant). Cells comprising an interferor can be produced by contacting the cells or by electroporation of the cells with a particular interferor molecule. In certain embodiments, cells comprising an interferer are generated through transfection (or transformation) wherein the interferor is encoded by a recombinant expression vector such as a plasmid or a viral vector.

Isolation: Separation and Detection

In certain embodiments, provided is a method to isolate a protein from a sample, the method comprising contacting the sample with a non-naturally occurring molecule comprising at least one self-association region present in the protein and isolating the resulting co-aggregated molecule-protein complex from the sample.

In certain embodiments, provided is a method to isolate a protein from a sample, the method comprising contacting the sample with a non-naturally occurring molecule comprising at least one self-association region isolated from the protein, wherein the self-association region is fused to a moiety that prevents aggregation of the self-association region and isolating the resulting co-aggregated molecule-protein complex from the sample.

In certain embodiments, provided is a method to isolate a protein from a sample comprising contacting the sample with a non-naturally occurring molecule comprising at least one self-association region isolated from the protein, wherein the self-association region is fused to a moiety that prevents aggregation of the self-association region so that the self-association region is in direct contact with the solvent, wherein the self-association region fused to the moiety and the protein are present and isolating the resulting co-aggregated molecule-protein complex from the sample.

In other words, provided is a method for the isolation of a protein from a sample comprising:
 contacting the protein with a non-naturally occurring molecule, which comprises part A and part B, wherein i) part A comprises a peptide, protein domain or agarose bead, preventing the aggregation of part B, and ii) part B, which comprises at least one self-association region, wherein the region consists of at least three contiguous amino acids, and wherein the region is isolated from the protein, and wherein a linker is optionally present between parts A and B; and
 isolating the resulting co-aggregated molecule-protein complex from the sample.

In still other words, provided is a method for the isolation of a protein from a sample comprising:
 contacting the protein with a non-naturally occurring molecule, which comprises part A and part B, wherein i) part A comprises a peptide, protein domain or agarose bead, preventing the aggregation of part B, and ii) part B, which comprises at least one self-association region, wherein the region consists of at least three contiguous amino acids, and wherein the region is isolated from the protein, and wherein a linker is optionally present between parts A and B, and wherein part B is in direct contact to the environment, wherein the molecule and protein are present; and
 isolating the resulting co-aggregated molecule-protein complex from the sample.

In still other words, provided is a method for the isolation of a protein from a sample comprising:
 contacting the protein with a non-naturally occurring molecule, which comprises part A and part B, wherein i) part A comprises a peptide, protein domain or agarose bead, preventing the aggregation of part B, and ii) part B, which consists of at least one self-association region, wherein the region consists of at least three contiguous amino acids, and wherein the region is isolated from the protein, and wherein a linker is optionally present between parts A and B, and wherein part B is in direct contact to the environment, wherein the molecule and protein are present; and isolating the resulting co-aggregated molecule-protein complex from the sample.

In still other words, provided is a method for the isolation of a protein from a sample comprising:

contacting the protein with a non-naturally occurring molecule, which comprises part A and part B, wherein i) part A comprises a peptide, protein domain or agarose bead, preventing the aggregation of part B, and ii) part B, which consists of at least one self-association region, wherein the region consists of at least three contiguous amino acids, and wherein the region is isolated from the protein, and wherein a linker is optionally present between parts A and B; and isolating the resulting co-aggregated molecule-protein complex from the sample.

Separation

In a further embodiment, the method for the isolation of at least one protein further comprises the separation of at least one protein from a sample.

One application of the separation of at least one protein from a sample is the removal (or depletion) of highly abundant proteins from a sample. Indeed, a major challenge in protein target discovery and validation is how to specifically dissect complex protein samples (e.g., plasma, urine, cerebrospinal fluid) and measure trace targets. The abundant proteins are often six to ten orders of magnitude more concentrated than low abundant proteins. Thus, highly abundant proteins must be removed to detect and measure trace proteins of medical importance. Since albumin, IgG, antitrypsin, IgA, transferrin and haptoglobin make up approximately 90% of the total protein content in human serum, there is a critical need for diagnostic tools to rapidly deplete these unwanted abundant proteins and unmask the less abundant, low molecular weight protein biomarkers. Several methods are already used in the art: 1) immunoglobulin G (IgG) as affinity reagents to capture and separate abundant protein targets, 2) immunoglobulin yolk (IgY) are IgG-like antibodies isolated from egg yolks of immunized birds, 3) pre-fractionation is used to separate a mixture of proteins into different fractions to remove certain proteins in the original mixture, and 4) protein A and protein G are bacterial cell wall proteins with a specificity to IgG antibodies, hence protein A and G affinity resins provide a removal of IgG and 5) IgG- and IgY-microbeads are used for protein detection.

Detection

In certain embodiments, the method for the isolation of at least one protein further comprises the detection of at least one protein in the molecule-protein complex.

Detection can be carried out by separating the interferor molecule-target protein complex by, for example, electrophoresis, column chromatography, filtration, electrostatic attraction, magnetic or paramagnetic attraction, mass spectrometry and the like.

The most broadly used biodetection technologies are based on the use of antibodies. Antibodies recognize and bind to other molecules based on their shape and physicochemical properties. Antibodies are highly suited for detecting small quantities of target proteins in the presence of complex mixtures of proteins. The invention shows that the use of interferor molecules (part B has the specificity and recognition for at least one specific protein) is an alternative for the use of antibodies (as the recognition element) for the specific capture of target proteins. Indeed, interferor molecules can be used in numerous applications in which antibodies typically are used. To name only a few, applications are envisaged in diagnosis, micro-analytics, forensics and in the specific detection of pathogens.

For the detection and separation applications of the invention, it is preferred that part B of the interferor molecule is bound to a carrier, which is herein designated as part A. A carrier can be a flat surface such as plastic or nitrocellulose or a chromatographic column but is preferably a bead such as microsphere beads. A general discussion on various types of beads and microspheres, which serve the purpose of being part A of the interferor molecules, is described on pages 9 and 10 of U.S. Pat. No. 6,682,940 and is herein specifically incorporated by reference.

In certain embodiments, part A of the interferer molecule is a carbohydrate type of carrier, e.g., cellulose or agarose. Part B can be covalently bound to the carbohydrate carrier with a cross-linking agent such as glutaraldehyde.

In certain embodiments, part A is a support such as cellulose, glass or a synthetic polymer. Covalent attachment between part A and part B can be carried out via amino acid residues of part B and an azide, carbodiimide, isocyanate or other chemical derivatives present on part A.

In certain embodiments, part A is a porous silanized glass micro bead. Part B can be covalently bonded to part A via its peptide amine groups (by Schiff reaction followed by reduction with sodium borohydride) to aldehyde groups formed by periodate oxidation of glycidoxypropylsilane groups chemically linked to the silica atoms (this coupling is described in Sportsman and Wilson (1980) *Anal. Chem.* 52:2013-2018).

In certain embodiments, the carrier part A is enveloped by a proteinaceous film to which part A is cross-linked (see claims 1-50 and examples relating to the carrier in U.S. Pat. No. 4,478,946).

In another specific embodiment, part A is a fluorescent bead such as a fluorescent latex particle. U.S. Pat. No. 4,550,017, and especially page 4 therein, the contents of which are incorporated herein by this reference, describes fluorescent compounds, which can be used for the manufacturing of fluorescent beads.

In another specific embodiment, the beads, part A, vary in size and may also contain or be impregnated with fluorescent dyes. Because of varying sizes and dyes of the beads, multiple proteins can be detected and quantitated in a single reaction. Procedures for the development of such beads are described in U.S. Pat. No. 6,159,748, the contents of the entirety of which are incorporated herein by this reference.

In yet another particular embodiment, the coupling between part A (the bead) and part B is via a poly(threonine), a poly(serine), dextran or poly(ethylene glycol). Examples 6, 7, 8 and 9 of U.S. Pat. No. 6,399,317, the contents of the entirety of which are incorporated herein by this reference, illustrate how this coupling can be carried out.

In yet another particular embodiment, part A is a magnetic bead. Magnetic beads, coupling between the magnetic beads and a protein agent and their uses are described on page 8 of application U.S. Pat. No. 6,489,092, the contents of the entirety of which are incorporated herein by this reference.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the invention, preferred methods and materials are described. For the purposes of the invention, the following terms are defined below.

The articles "a" and "an" are used herein to refer to one or to more than one (i.e., to at least one) of the grammatical object of the article. By way of example, "a target protein" means one target protein or more than one target protein.

As used herein, the term "about" refers to a quantity, level, value, dimension, size, or amount that varies by as much as 30%, preferably by as much as 20%, and more preferably by as much as 10% to a reference quantity, level, value, dimension, size, or amount.

"Bifunctional cross-linking reagent" means a reagent containing two reactive groups, the reagent thereby having the ability to covalently link two elements such as part A and part B of the interferer molecule. The reactive groups in a cross-linking reagent typically belong to the classes of functional groups including succinimidyl esters, maleimides and haloacetamides such as iodoacetamides. Throughout this specification, unless the context requires otherwise, the words "comprise," "comprises" and "comprising" will be understood to imply the inclusion of a stated step or element or group of steps or elements but not the exclusion of any other step or element or group of steps or elements.

By "expression vector" or "recombinant vector" is meant any autonomous genetic element capable of directing the synthesis of an interferor molecule encoded by the vector. Such expression vectors are known to practitioners in the art.

By "derivative" is meant an interferor molecule that has been derived from the basic sequence by modification, for example, by conjugation or complexing with other chemical moieties (e.g., pegylation) or by post-translational modification techniques as would be understood in the art. The term "derivative" also includes within its scope alterations that have been made to a parent sequence including additions or deletions that provide for functionally equivalent molecules.

By "effective amount," in the context of modulating an activity or of treating or preventing a condition, is meant the administration of that amount of an interferer molecule to an individual in need of such modulation, treatment or prophylaxis, either in a single dose or as part of a series, that is effective for modulation of that effect or for treatment or prophylaxis of that condition. The effective amount will vary depending upon the health and physical condition of the individual to be treated, the taxonomic group of individuals to be treated, the formulation of the composition, the assessment of the medical situation, and other relevant factors. It is expected that the amount will fall in a relatively broad range that can be determined through routine trials.

By "isolated" is meant material that is substantially or essentially free from components that normally accompany it in its native state. For example, an "isolated polypeptide," as used herein, refers to a polypeptide, which has been purified from the sequences which flank it in a naturally occurring state, e.g., a self-association sequence that has been removed from the sequences that are normally adjacent to the sequence. A self-association sequence (optionally coupled to a moiety that prevents aggregation) can be generated by amino acid chemical synthesis or can be generated by recombinant production.

The term "oligonucleotide," as used herein, refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). An oligonucleotide is typically rather short in length, generally from about 10 to 30 nucleotides, but the term can refer to molecules of any length, although the term "polynucleotide" or "nucleic acid" is typically used for large oligonucleotides. The term "polynucleotide" or "nucleic acid," as used herein, designates mRNA, RNA, cRNA, cDNA or DNA. The term typically refers to oligonucleotides greater than 30 nucleotides in length.

The term "recombinant polynucleotide," as used herein, refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "operably linked" is meant that transcriptional and translational regulatory nucleic acids are positioned relative to a polypeptide-encoding polynucleotide in such a manner that the polynucleotide is transcribed and the polypeptide is translated.

The terms "subject" or "individual" or "patient," used interchangeably herein, refer to any subject, particularly a vertebrate subject, and even more particularly, a mammalian subject, for whom therapy or prophylaxis is desired. Suitable vertebrate animals that fall within the scope of the invention include, but are not restricted to, primates, avians, fish, reptiles, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). However, it will be understood that the aforementioned terms do not imply that symptoms are present.

By "pharmaceutically acceptable carrier" is meant a solid or liquid filler, diluent or encapsulating substance that can be safely used in topical or systemic administration to a patient.

"Polypeptide," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally occurring amino acid polymers.

By "recombinant polypeptide" is meant a polypeptide made using recombinant techniques, i.e., through the expression of a recombinant or synthetic polynucleotide. When the chimeric polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The term "sequence identity," as used herein, refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the invention, "sequence identity" will be understood to mean the "match percentage" calculated by the DNASIS computer program (Version 2.5 for windows; available from Hitachi Software Engineering Co., Ltd., South San Francisco, Calif., USA) using standard defaults as used in the reference manual accompanying the software. "Similarity" refers to the percentage number of amino acids that are identical or constitute conservative substitutions. Similarity may be determined using sequence comparison programs such as GAP (Deveraux et al. 1984, Nucleic Acids Research 12:387-395). In this way, sequences of a similar or substantially different length to those cited herein might be compared by insertion of gaps into the alignment, such gaps being determined, for example, by the comparison algorithm used by GAP.

The term "transformation" means alteration of the genotype of an organism, for example, a bacterium, yeast or plant, by the introduction of a foreign or endogenous nucleic acid. Vectors for transformation include plasmids, retroviruses and other animal viruses, YACs (yeast artificial chromosome), BACs (bacterial artificial chromosome) and the like. By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated.

A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In certain embodiments, the vector is preferably a viral or viral-derived vector, which is operably functional in animal and preferably mammalian cells. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene that confers resistance to the antibiotic hygromycin B.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, useful methods and materials are described below. The materials, methods, and examples are illustrative only and not intended to be limiting. Other features and advantages of the invention will be apparent from the detailed description and from the claims.

EXAMPLES

Example 1

Design of a Synthetic Peptide Interferor Molecule

We constructed an interferor molecule, wherein part B consists of three synthetic self-association regions with short linkers of two amino acids (STLIVL-QN-STVIFE-QN-STVIFE; SEQ ID NO:1) interconnecting the self-association regions. The three self-association regions are hexapeptides, which have a strong tendency to aggregate, see FIG. 1 for the design of the interferor molecule. Note: in the text of this invention, all amino acid sequences are depicted starting from the amino-terminal part and read in the direction of the carboxy-terminal part—thus, "STLIVL" (SEQ ID NO:2) reads as "NH$_2$—STLIVL (SEQ ID NO:2)—COOH"). Part B of the synthetic interferer molecule was N-terminally fused to a moiety (part A) that prevents aggregation and brings the self-association regions in direct contact with the environment (here the cytosol of E. coli). (FIG. 1 depicts the structure of the synthetic interferor design.) The moiety is the NusA protein, which is frequently used as a solubilizing tag in recombinant protein production.[13] The resulting synthetic interferor molecule (A-B structure) could be made and purified in a recombinant way in E. coli.

We have shown that over-expression of the synthetic interferer molecule (without any specific self-association sequence specific for a particular E. coli protein) does not prevent bacterial growth. Therefore, BL21 E. coli cells were transformed with the synthetic interferor construct present in the pETM60 plasmid (gift from G. Stier, EMBL). In the latter plasmid, the interferors are under control of the chimeric T7 promoter (see materials and methods section). Recombinants were grown to a density of 0.6 OD, the interferor was expressed upon the addition of 0.5 µM IPTG for three hours at 37° C. and the bacterial suspension was plated on agar plates. The plates were inspected after 12 hours incubation at 37° C. and showed abundant bacterial growth.

In a next step, a flexible linker sequence ("KPGAAKG" (SEQ ID NO:3)—depicted as "linker" in FIG. 1) was coupled to the COOH-terminus of the synthetic interferor construct to allow fusion of self-association sequences derived from a target protein.

Example 2

Protein Interference in Prokaryotes

In the present example, E. coli proteins were chosen to be down-regulated, of which a functional protein interference confers a selectable trait. Target proteins from the E. coli proteome were selected with a cytosolic localization and the presence of an aggregation region with a suitable high TANGO score. Since conditional auxotrophy for a single amino acid can conveniently be tested using growth media with controlled composition, we selected four candidate enzymes involved in the synthesis of isoleucine (UniProt[15] entry: ILVI_ECOLI), methionine (UniProt[15] entries: METE_ECOLI and METK_ECOLI) and leucine (UniProt[15] entry: LEU1_ECOLI). The self-association sequences based on the TANGO prediction score of the four target proteins was for ILVI_ECOLI: "GVVLVTSG," (SEQ ID NO:4) TANGO score: 44; for METE_ECOLI: "LLLTTYF," (SEQ ID NO:5) TANGO score: 32; METK_ECOLI: "LTLLV," (SEQ ID NO:6) TANGO score: 20; and LEU1_ECOLI: "LAFIG," (SEQ ID NO:7) TANGO score: 15.

The genetic information for the synthetic interferor molecule of Example 1 was fused to the DNA-sequence encoding the respective self-association regions of the four biosynthetic enzymes, resulting in four specific interferor molecules. To show in vivo protein interference (which is essentially a co-aggregation between the specific interferor (for a biosynthetic enzyme) and the biosynthetic enzyme itself) we proceeded as follows. E. coli were transformed with the plasmid comprising the respective interferor constructs and grown in rich medium until the start of the exponential growth phase, when interferor protein expression was induced with IPTG (isopropyl-beta-D-thiogalactopyranoside). Protein expression was allowed to proceed at 37° C., cells were harvested, washed with a salt solution to remove excess IPTG and rich medium and plated on agar plates containing minimal M9 medium completed with the twenty naturally occurring amino acids (called M9 complete medium) and on minimal M9 medium with all amino acids except the one for which auxotrophy is being tested (called M9 select). It was shown that for three out of four targeted enzymes, a complete functional knock-out could be achieved, i.e., conditions were found in which the bacteria formed colonies on M9 complete but not on M9 select agar plates.

Expression of the interferor constructs and their exclusive presence in the insoluble phase of the cell-lysate was confirmed by western blot. For the four enzymes tested here, a clear relationship is observed between their sensitivity for the co-aggregation approach and their predicted aggregation propensity according to the TANGO algorithm, further confirming the quality of the TANGO predictions as well as their relevance in a functional cellular context. The ILVI protein, which has the highest TANGO score, was almost completely knocked out by the leaky expression from the T7 promoter in the absence of any IPTG, and one hour of induced over-expression leads to a full functional knock-out. The METE and METK enzymes display an intermediate TANGO score and were not affected by a single hour of over-expression of the interferor. However, after three hours of IPTG induction, the function was lost completely and no colony formation could be detected. The weakest aggregation score was observed for the LEU1 enzyme and over-expression in this case produced only a modest down-regulation of its activity. Remarkably, the functional knock-out of the targeted enzymes is reversible. When cells loaded with a high level of over-expressed interferer material were plated on LB agar, they displayed normal colony growth. When these colonies were copied into M9 select, normal growth was again observed. This indicates that during colony growth, the aggregates were lost, reinstating the cellular network to normal.

Example 3

Protein Interference of Targets Comprising Self-Association Regions with a Low Self-Association Score Self-association regions are often flanked or contain charged residues such as R, K, D and E but also P and G (so-called gatekeeper amino acid residues) (see Rousseau, Serrano and Schymkowitz (2006), "How Evolutionary Pressure Against Protein Aggregation Shaped Chaperone Specificity," *J. Mol. Biol.*, doi:10.1016/j.jmb.2005.11.035). These gate keeper residues reduce the self-association propensity of the sequences they are associated to. In order to optimize the sensitivity of the B-part of an interferer molecule to co-aggregate with a given target protein, the self-association region of the target protein that is included in the B-part of the interferor can be mutated so that the above-mentioned residues are replaced by aggregation-promoting residues such as L, V, I, F, W, Y. Other residues that can increase the self-association propensity of the self-association region can also be included. The mutated self-association region (derived from the target protein), which is included in the B-part of the interferer molecule, has a sequence homology of at least 60%, preferably at least 70%, more preferably at least 80% and most preferably at least 90%, with the self-aggregation region of the target protein.

In addition, some amino acids are neutral in terms of aggregation and replacing the amino acids with amino acids that favor aggregation will also increase the self-association tendency of a region (for example, S, T, C, but also Q, N, H, M can be replaced by aggregation prone residues such as L, V, I, F, W, Y). These optimized integrator molecules increase the protein interference of targets with a predicted low aggregation score. In Example 2, we showed that the protein interference of the LEU1 enzyme of *E. coli* is less efficient. In this example, we optimize the interferor molecule with a specificity for the LEU1 enzyme. The identified self-association sequence in LEU1 is "LAFIG" (SEQ ID NO:7). The latter sequence is flanked by the gatekeeper residues " . . . DYDLE-ALAFIGKQQEE . . . " (SEQ ID NO:8).

Therefore, in order to mutationally enhance the target sequence, we employ a strategy based on degenerate pcr as follows: complementary primers are designed that have an overlap of 20 to 25 bp on each side of the codon that will be mutated to allow efficient annealing of the primers to the template. A degenerate codon is introduced by incorporating an equimolar ratio of the four bases during primer synthesis (a so-called NNS codon). Using the Quickchange PCR protocol with this degenerate primer, a library containing the 20 point mutations of the flanking position is obtained. This library is amplified in Top10 cells (Invitrogen) and the plasmid DNA purified using the miniPrep kit (Qiagen). To test if knockout efficiency is increased, mutant interferors (design is carried out as in Example 2) against the LEU1 target are transformed into BL21 cells (Invitrogen) and plated on LB agar plates. In a 96-well plate containing 0.2 mL LB+antibiotic per well, each well is inoculated by picking individual colonies. The plate is incubated at 37° C. until an OD of 0.6 is reached, when expression of the mutant interferors is induced by adding 0.5 µM IPTG for three hours at 37° C. The complete content of each well (except 1 µL) is plated on a selective minimal medium that contains all amino acids except leucine. For clones that show different gradations of impaired growth on the selective plates, TempliPhi reagent (GE Health Science) is added for DNA amplification and the plate is transferred to the sequencing facility. The sequence information provides us the full spectrum of optimized LEU1-mutated interferor molecules.

Example 4

Use of Interferor Molecules for the Depletion of Immunoglobulin G from Serum

In this depletion experiment, an agarose bead is chosen as a moiety (part A) to which self-association regions derived from a target protein are fused via amino reactive chemical linking. Such agarose materials are commercially available, such as NHS-activated Sepharose™ 4 Fast Flow from GE Healthcare. Human immunoglobulin G has two strong tango regions ((I) IIVAVVIATAVAAIVAAVVALIY (SEQ ID NO:9) and (II) LTVLLLLASA (SEQ ID NO:10)) that can be used as self-association regions. Since peptide expense scales with length in amino acids, peptides are designed to contain ten amino acid fractions from the first target region. The target sequences (self-association regions) are preceded with the linker sequence ADPRGAAEGA (SEQ ID NO:11) and synthesized with unprotected ends to maintain the reactive N-terminal amino group. The designed sequences are (a) ADPRGAAEGAIIVAVVIATA (SEQ ID NO:12), (b)

ADPRGAAEGAVVIATAVAAI (SEQ ID NO:13), (c) ADPRGAAEGAIVAAVVALIY (SEQ ID NO:14) (a, b and c comprise decapeptides derived from the strong tango region I), and (d) ADPRGAAEGALTVLLLLASA (SEQ ID NO:15) (comprises tango region II). For depletion, 10 ml of serum is incubated with 1 mg of immobilized peptide at 25, 30, 37 and 45° C. for one hour. Agarose beads are collected by centrifugation and the serum is removed. Agarose beads are washed in PBS buffer in order to remove remaining impurity. The beads are subsequently transferred to SDS buffer and incubated at 95° C. for ten minutes and vortexed extensively. The presence of IgG is investigated using SDS-PAGE. The identity of target is confirmed using mass spectrometry.

Example 5

Use of Interferor Molecules for Detection

Interferor molecules were designed for the specific detection of three commercially available recombinant proteins (citrate synthase from porcine heart (Roche), beta-galactosidase from *E. coli* (Sigma) and glucose-6-phosphate dehydrogenase from *Leuconostoc mesenteroides* (Sigma)). Thereto, in a first step, self-association regions were determined with the TANGO algorithm from the following target proteins:
  (a) citrate synthase (CISY_PIG): "ALFWLLVT" (SEQ ID NO:16; TANGO score 60);
  (b) beta-galactosidase (BGAL_ECOLI): "AVIIWSLGN" (SEQ ID NO:17; TANGO score 30) and "ALAVVLQ" (SEQ ID NO:18; TANGO score 42); and
  (c) glucose-6-phosphate dehydrogenase (G6PD_LEUME): "AFVDAISAVYTA" (SEQ ID NO:19; TANGO score 41).

In a next step, biotin was amino-terminally coupled to the four different self-association regions resulting in four different interferor molecules: (i) biotin-ALFWLLVT (SEQ ID NO:16) with a specificity for citrate synthase; (ii) biotin-AVIIWSLGN (SEQ ID NO:17) and biotin-ALAVVLQ (SEQ ID NO:18) with a specificity for beta-galactosidase; and (iii) biotin-AFVDAISAVYTA (SEQ ID NO:19) with a specificity for glucose-6-phosphate dehydrogenase. Biotinylated peptides were acquired from Jerine Peptide Technologies. Note that the interferor design: biotin—self-association region corresponds with the A-B structure wherein biotin (part A) prevents the aggregation of the self-association region (part B) and brings the self-association region in direct contact with the solvent (PBST) wherein the biotin-self-association region is present.

Individual dot blots were prepared by spotting 0.3 mg of each target protein on nitrocellulose membrane, followed by air drying and overnight incubation in 1% BSA-PBST (PBS with 0.1% Tween-20) to block non-specific binding sites. The membrane was immersed in a 10 mM solution of biotinylated detection peptide and incubated for three hours at room temperature with agitation. After repeat washing with buffer, the binding of the peptide to the protein was confirmed by visualization of the biotin moiety using streptavidin-HRP (Horse Radish Peroxidase, Pierce) and chemiluminescence detection using a CCD camera system.

Example 6

Use of Interferor Molecules Against Murine VEGF for the Treatment of Pathological Retinal Angiogenesis Retinal neovascularization is a major cause of blindness in the world and pathological retinal angiogenesis is a final common pathway leading to vision loss in diseases such as retinopathy of prematurity (ROP), diabetic retinopathy and age-related macular degeneration. It is known that vascular endothelial growth factor (VEGF) is one of the key players in the development of pathological angiogenesis. We studied the effect of interferor molecules against VEGF in two murine-induced retinopathy models. In a first model, neonatal mice (with an immature retinal vasculature) are exposed to hyperoxia, resulting in obliteration of the developing blood vessels supplying oxygen to the retina. When the mice are then returned to normoxia, the retina, distal to the occluded vessels, becomes ischemic, inducing VEGF production and ultimately resulting in reproducible and quantifiable proliferative retinal neovascularization (the model is detailed in E. A. Pierce et al. (1995), *Proc. Natl. Acad. Sci.* 92(3)905-9, see experimental procedures on page 905—mouse model). In short, mouse pups of seven days (P7) together with their nursing mothers, are subjected to hyperoxia (75% oxygen) in specially designed oxygen chambers for five days, without opening the cages. On P12, the animals are returned to room air until P17, when the retinas are assessed for maximal neovascular response. On P12, half of the animals are treated with an interferer molecule against VEGF and half are left untreated. Half of the treated mice receive VEGF interferor by way of intravitreous injection while the other half of the treated group receive VEGF interferer by way of periocular injection (the periocular or intravitreous injection is carried out as described in J. Shen et al. (2006), *Gene Therapy*, advance online publication 29 September). Three different interferer molecules against the murine VEGF165 isoform are used in a concentration range of 1 to 100 μg/ml.
  (a) REAG-FLLSWVHWTLALLLYLHH-GGEERAG (SEQ ID NO:20); this interferor molecule has the A-B-A' structure of an interferor molecule. The self-association region derived from murine VEGF165 (underlined) is flanked by solubilizing regions A (REAG (SEQ ID NO:21) and GGEERAG (SEQ ID NO:22)), or in other words, the regions A and A' prevent the aggregation of the self-association region (B-part of the interferor molecule).
  (b) STVIIE-GGAG-NHVTLS-GGAGQ-FLLSWVHWTLALLLYLHH-GERAG (SEQ ID NO:23); this interferer molecule has the B-A structure of an interferer molecule. The solubilizing part A (GERAG (SEQ ID NO:24)) is shown in italics. The B-part has the following structure: STVIIE (SEQ ID NO:25; =synthetic self-association region)—GGAG (SEQ ID NO:26; =a linker)—NHVTLS (SEQ ID NO:27; =synthetic self-association region)—GGAGQ (SEQ ID NO:28; =a linker)—FLLSWVHWTLALLLYLHH (SEQ ID NO:29; =the self-association region derived from murine VEGF 165).
  (c) STVIIE-GGAG-FLLSWVHWTLALLLYLHH-GERAG (SEQ ID NO:30); this interferor molecule has the B-A structure of an interferor molecule. The solubilizing part A (GERAG (SEQ ID NO:24)) is shown in italics. The B part has the following structure: STVIIE (SEQ ID NO:25; =synthetic self-association region)—GGAG (SEQ ID NO:26; =a linker between the self-association regions)—FLLSWVHWTLALLLYLHH (SEQ ID NO:29; =the self-association region derived from murine VEGF165).

On P17, anesthetized mice are perfused through the left ventricle with 1 ml of phosphate buffered saline containing 50 mg of $2 \times 10^6$ molecular weight fluorescein-dextran. The eyes are removed and fixed in 4% paraformaldehyde for three (right eye) or 24 (left eye) hours. Of the right eyes, lenses are removed and peripheral retinas cut to allow flat mounting with glycerol-gelatin. The flat-mounted retinas are analyzed by fluorescence microscopy. The left eyes are embedded in paraffin and serial 6 μm sections are cut sagittally throughout the cornea, parallel to the optic nerve, and stained with hematoxylin-eosin. The proliferative neovascular response is quantified by counting the number of new vessels (=tufts) and the number of endothelial cells extending from the internal limiting membrane of the retina into the vitreum on the stained sagittal cross-sections. The angiographic technique using fluorescein-dextran perfusion is used in conjunction with this counting method for rapid screening of retinas or as an alternative grading system for quantitative evaluation. In a second model, retinal neovascularization is experimentally mimicked by laser-induced venous thrombosis in the retina. The model is described in Y. Saito et al. (1997), *Curr. Eye Res.* 16(1):26-33. Chi-Chun Lai et al. (2005), *Acta Ophtalmologica Scandinavica* 83:590-594, describe in the materials and methods section on pages 591-592 that the model can be quantitated. Application of the VEGF interferor molecules is carried out as described herein before.

Example 7

Protein Interference in a Human Cell Line

The modulation of apoptosis (induction or suppression) is easy to monitor in a cellular system. It is known that staurosporin induces apoptosis in a p53-dependent manner. Thus, the down-regulation of p53 or the down-regulation of proteins that enhance the function of p53 (e.g., ASPP1) suppresses staurosporin-induced apoptosis in animal (e.g., human) cell lines. Recombinant expression vectors that encode interferor molecules are constructed based on the design of the synthetic interferer molecule described in Example 1, except that the A part, the NusA protein, is changed to the green fluorescent protein (GFP) and that the promoter is a constitutive mammalian promoter such as the actin or the CMV promoter. The self-association sequence for p53 is ILTIITLE (SEQ ID NO:31; which has a tango score of 72) and this sequence is additionally comprised into the B part of the synthetic interferer leading to an interferor molecule with a specificity for p53. The self-association sequence for ASPP1 is MILTVFLSN (SEQ ID NO:32; which has a tango score of 63) and this sequence is additionally comprised into the B part of the synthetic interferer molecule leading to an interferor molecule with a specificity for ASPP1. HeLa cells are cultured and transfected with the recombinant vectors. The GFP (A part) allows the visualization of the over-expressed interferor molecules. Addition of 1 μM staurosporin to transfected and non-transfected control cells induces a differential apoptotic response.

Example 8

Protein Interference of Vascular Endothelial Growth Factor (VEGF) in Zebra Fish

Interferor molecules were developed that directed to zebra fish VEGF. Specific inactivation (through aggregation) of the secreted VEGF can be followed by a disturbance of the vascular development in zebra fish embryos.

In a first step, the self-association regions present in the zebra fish VEGF protein were determined with the TANGO algorithm. The aggregating region with the highest TANGO-score is NH$_2$—FLAALLHLSA-COOH (SEQ ID NO:33).

Based on this self-association sequence, we developed four synthetic interferer molecules:

```
                                              (SEQ ID NO: 34)
    Interferor A:   NH2-RLFLAALLRFLAALLHLSAR-COOH;

(SEQ ID NO: 35)
    Interferor B:   NH2-RFLAALLHLSARLFLAALLR-COOH;

(SEQ ID NO: 36)
    Interferor C:   NH2-RYLAILAGIRLFLAALLR-COOH;

(SEQ ID NO: 37)
    Interferor D:   NH2-RYLAILAGIRFLAALLHLSAR-COOH;

(SEQ ID NO: 38)
    Interferor E    (NH2-EALVVYLIQLAGR-COOH)
``` served as a control sequence and is derived from a sequence outside this high TANGO region.

Note that interferors A, B and D comprise the whole TANGO region, while interferor C comprises only a part of the TANGO region. The sequences derived from the TANGO regions are underlined.

These interferer molecules were added to the medium of transgenic Tg(fli1:EGFP)$^{y1}$ zebra fish embryos at different concentrations. Transgenic Tg(fli1:EGFP)$^{y1}$ zebra fish express enhanced Green Fluorescent Protein (GFP) in their endothelial cells (the fish are described in N. D. Lawson and B. M. Weinstein (2002), *Dev. Biol.* 248, 307-318, are provided by the Zebra fish International Resource Center (University of Oregon) and are maintained as described in the zebra fish book, a guide for the laboratory use of zebra fish (*Danio rerio*), Univ. Oregon Press, Eugene, 1994).

Dechorionated embryos of 20 hours post-fertilization (hpf) were arrayed in 24-well plates (ten embryos/well) and exposed at several concentrations of the selected interferer molecules (starting at 50 μM) for 24 hours. Live embryos were analyzed at 28 and 48 hpf (hours post-fertilization) using confocal imaging, which was performed using a Zeiss laser-scanning microscope LSM510.

Although monitoring the development of different vascular structures, we paid particular attention to (i) the structure of the dorsal aorta (DA), posterior cardinal vein (PCV), (ii) the sprouting of the intersomitic vessels (ISV) and the formation of the vascular plexus (PV) in the posterior region of the trunk. A summary of the dose-dependant experiments is shown in Table 1. It is clear that interferors A and C induce clear vascular defects in the developing zebra fish larvae. Surprising is the fact that the interferor molecules are taken up by the zebra fish larvae through the skin and that no injection of the interferors is necessary. Interferors B and D need to be administered at still lower concentrations in order to be able to monitor the specific vascular defects.

Example 9

Protein Interference in the Yeast *Saccharomyces cerevisiae*

We have used the knock-down of the yeast Ura3 enzyme to show that protein interference works in eukaryotes because targeted inactivation (through aggregation) of the Ura3 protein gives an easy readout. The *S. cerevisiae* Ura3 enzyme is an essential enzyme involved in the uracil biosynthesis pathway. Hence, *S. cerevisiae* mutants lacking the URA3 gene are not able to grow on medium without uracil but growth can be restored by addition of uracil to the medium. In a first step, the self-associations regions present in the Ura3 protein were determined with the TANGO algorithm. The self-association region (or the aggregation region) with the best TANGO score is NH$_2$-VIGFIAQ-COOH (SEQ ID NO:39; TANGO score: 74). This peptide sequence was used to generate an interferor expression construct. To clone the self-association sequence encoding this peptide in frame with the synthetic interferor construct (see Example 1), we used the following two oligonucleotides:

URA3aggregatorFor:
(SEQ ID NO: 40)
5' CC<u>TCTAGA</u>ATGAAAGAAATTTTGGCTGTAG 3';
and URA3aggregatorRev:
(SEQ ID NO: 41)
5' CC<u>GTCGAC</u>*TTA* AGC TTG AGC AAT AAA GCC GAT AAC
GCCAGCAGCGCCCGGTTTAGCAGC 3'.

The XbaI and SalI restriction sites are underlined. The start codon of the NusA protein is highlighted in bold. The stop codon is depicted in italics and the sequence encoding the seven Ura3 amino acids is depicted in bold.

As a template for the PCR, we have used the pETM60 plasmid (gift from G. Stier, EMBL) that contains the NusA protein coupled to the synthetic interferor/linker construct (see Example 1). This vector contains a T7 promoter, confers kanamycin resistance and provides an N-terminal expression tag of six histidines. The resulting PCR product was subcloned in the pBEVY/GT vector (C. A. Miller 3$^{rd}$, M. A. Martinat and L. E. Hyman (1988), *Nucleic Acids Res.* 26:3577-3583) using the XbaI and SalI restriction sites. In this vector, the "NusA-synthetic interferor-linker-Ura3 self-association sequence"—expression cassette was under the control of the *S. cerevisiae* GAL1/10 promoter. The selection marker of this vector is the TRP1 gene.

Figure 2:
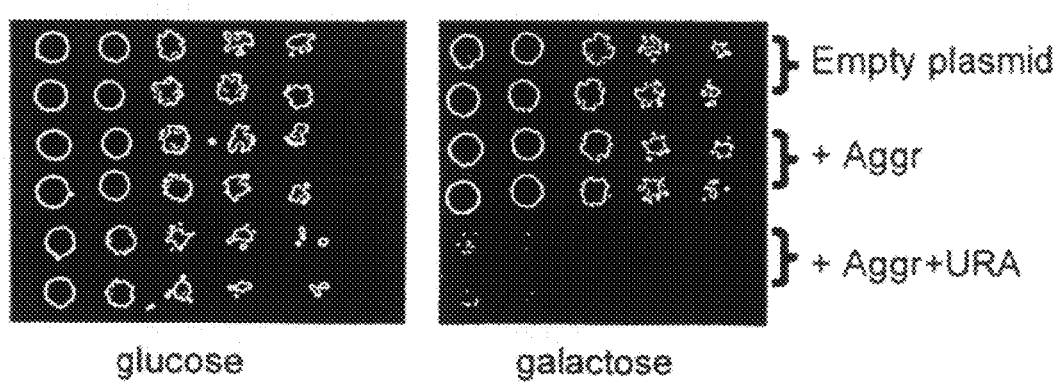
FIG. 2: *S. cerevisiae* cells with an endogenous wild-type copy of URA3 were transformed with the empty plasmid, the plasmid with only the aggregator sequence or the plasmid with the aggregator-Ura3 fusion construct. The cells were grown overnight in glucose-containing medium, washed and then plated on either glucose-(left) or galactose-(right) containing medium. Five µl of ten-fold dilutions are plated ($OD_{600}$=1 as highest concentration).

Sequence verified constructs with and without the DNA encoding the seven Ura3 amino acids (derived from the self-association region) were introduced into the *S. cerevisiae* strain PVD2 by transformation and selection of transformants was based on trp1 complementation. The PVD2 strain is derived from the W303-1A strain (B. J. Thomas and R. Rothstein (1989), *Cell* 56:619-630) but the PVD2 strain is transformed with wild-type alleles of both HIS3 and URA3. The PVD2 strain is still auxotrophic for leucine (LEU2), tryptophan (TRP1) and adenine (ADE2). Transformants were selected on SDglu-Trp medium (minimal yeast medium with 2% glucose but without tryptophan). Colonies were re-streaked on fresh SDglu-Trp plates for single colonies. Two independent colonies were grown overnight in liquid SDglu-Trp medium. The OD$_{600}$ of the culture was then adjusted to one and 5 microliters of a ten-fold serial dilution were spotted on SDglu-Ura-Trp (SD-medium with 2% glucose but without uracil and without tryptophan) or SDgal-Ura-Trp (SD-medium with 2% galactose but without uracil and without tryptophan) plates. The result of this experiment is shown in FIG. 2. This experiment has been repeated three times with similar results. Expression of the empty pBEVY/GT vector or the vector expressing only the NusA-synthetic interferor construct (without a self-association sequence from ura3) does not show any growth inhibition on medium without uracil. Expression of the NusA-synthetic interferor-Ura3 association region construct, however, strongly inhibits growth on medium without uracil (when uracil is added to the growth medium, there is no growth defect), showing that the endogenous Ura3 protein is specifically inactivated by protein interference.

Example 10

Protein Interference in the Yeast *Candida albicans*

*Candida albicans* causes 40% of the fungal infections in humans. This commensal possesses a number of virulence factors. Apart from the capacity to adhere to all kinds of plastics (a major problem in intensive care units) or the production of lipases and proteinases, it is the capacity to adopt various morphologies that has been studied most extensively because it is one of the major virulence factors. Many transcription factors can induce the transition from yeast-like cells to hyphae or pseudohyphae. Other transcription factors are required to keep the cells in the yeast-like form. One example of such a repressor of hyphal formation is Tup1. As an example of protein interference in *Candida albicans*, we have used the Tup1 protein as a target. Down-regulation of the biological function of Tup1 should induce hyphal formation. In a first step, the self-association regions present in the Tup1 protein were determined with the TANGO algorithm. The self-association region (or the aggregation region) with the best TANGO score (TANGO score: 30) is NH$_2$-VISVAVSL-COOH (SEQ ID NO:42). This peptide was used to generate an interferor expression construct. To clone the self-association sequence encoding this peptide in frame with the synthetic interferor construct of Example 1, we used the following two oligonucleotides:

TUP1aggregatorFor:
(SEQ ID NO: 43)
5'AT<u>TGTACA</u>AATATCCGTATGTGCCTGACTACGCAATGGCTCAGTGGCA GAAC 3';
and TUP1aggregatorRev:
(SEQ ID NO: 44)
5' GC<u>GCTAGC</u>*TTA* AGC TAG GGA TAC AGC GAC TGA GAT GAC

GCCAGCAGCGCCCGGTTTA 3'.

The BsrGI and NheI sites are underlined. The stop codon is depicted in italics and the reverse sequence encoding the target peptide is depicted in bold.

Figure 3:
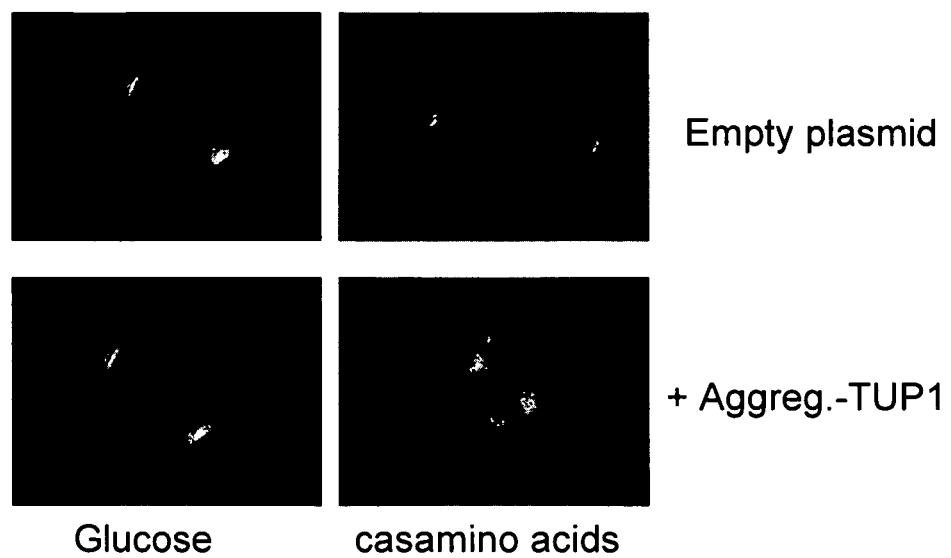
FIG. 3: *C. albicans* cells with two endogenous wild-type copies of TUP1 were transformed with the empty plasmid and the plasmid with the interferor-Tup1 fusion construct. The cells were grown overnight in glucose containing medium, washed and then 20 colonies were plated on either glucose-(left) or casamino acid-(right) containing medium. The upper panel are those with an empty plasmid, the lower panel with the interferor construct ("+aggreg.—TUP1" means interferor—TUP1 construct). Pictures were taken after four days of growth.

We have used the pETM60 plasmid containing the NusA-synthetic interferer construct (from Example 1) as a template for the PCR. The resulting PCR product was subcloned in the pPCK1-GFP plasmid (C. J. Barelle, C. L. Manson, D. M. MacCallum, F. Odds, N. A. R. Gow, and A. J. P. Brown (2004), *Yeast* 21:333-340) using the BsrGI and NheI restriction sites. In this vector, the interferer construct was cloned in frame with the GFP gene present on the vector and the resulting interferer expression cassette "GFP-synthetic interferor-linker-"Tup1 self-association region") is under the control of the PCK1 promoter. In the latter construct, green fluorescent protein (GFP) is replaced by NusA and GFP serves as part A of the interferer molecule. The PCK1 promoter is strongly induced in casamino acids-containing medium and repressed in glucose-containing medium (C. E. Leuker, A. Sonneborn, S. Delbruck, J. F. Ernst (1997), *Gene* 192:235-240). Sequence-verified plasmids were then transformed into the *C. albicans* strain CAI4 (W. A. Fonzi and M. Y. Irwin (1993), *Genetics* 134:717-728). Transformants were selected on SDglu-ura (yeast minimal medium comprising 2% glucose but without uracil). The transformants were grown overnight in glucose containing minimal medium, the cells were diluted to obtain about 20 cells/100 microliter and this volume was plated on SDglu-ura or SDcasamino acid-ura agar plates. Colony morphology was scored after four and six days of growth (see FIG. 3). As can be seen in FIG. 3, down-regulation of Tup1 occurs in medium with casamino acids and hyphal formation is clearly visible at the edge of the colonies. Hyphal formation is not seen in the control transformants (pPCK1-GFP plasmid without interferor expression cassette) or on the medium-comprising glucose. The example shows that the endogenous Tup1 is specifically inactivated by protein interference.

Example 11

Application of Protein Interference in Plants

We demonstrate protein interference in tobacco BY2-cells by using already transformed BY2-cells with several GFP-fusion genes (the genes are depicted in Table 2). A list of the *Arabidopsis thaliana* genes, together with their corresponding identified self-association regions and tango scores, is depicted in Table 2.

Specific interferor molecules against each of the targets of Table 2 are designed based on the synthetic interferor molecule described in Example 1, except that the NusA protein is changed by the Red Fluorescent Protein (RFP) and that the B part additionally comprises the specific self-association regions of the targets depicted in Table 2.

Constructs encoding the specific interferor molecules are introduced in appropriate vectors for over-expression using the Gateway™ technology (Invitrogen Life Technologies). To this end, a set of Gateway-compatible binary vectors for plant transformation was developed. For over-expression, the pK7WGD2 vector is used in which the gene is put under the control of the p35S promoter. For plant cell transformations, the ternary vector system is applied. The plasmid pBBRIMCS-5.virGN54D is used as a ternary vector. The binary plasmid is introduced into *Agrobacterium tumefaciens* strain LBA4404 already bearing the ternary plasmid by electro-transformation. Fresh BY-2 culture is established before the transformation with the particular construct. Five-day-old BY-2 is inoculated 1:10 and grown for three days (28° C., 130 rpm, dark). The liquid culture of *Agrobacterium tumefaciens* transformed with pK7WGD2-GUS (control vector), pK7WGD2-interferor 1 (e.g., specific for aurora 1), pK7WGD2-interferor 2 (e.g., specific for aurora 2), etc. Etcetera is established two days before the transformation of BY-2. A loopful of bacteria from the solid medium is inoculated in 5 ml of liquid LB medium with the antibiotics (rifampicin, gentamycin, streptomycin and spectinomycin). The culture is grown for two days (28° C., 130 rpm). The transformation of BY-2 is performed in empty petri dishes (Ø4, 6 cm) with the co-cultivation method. Three-day-old BY-2 (3 ml) is pipetted into plate and either 50 or 200 µl of bacterial suspension was added. The plates are gently mixed and left to stand in the laminar bench in the dark for three days. After co-cultivation, the cells are plated on the solid BY-2-medium with the selections (50 µg/ml kanamycin, 500 µg/ml vancomycin, and 500 µg/ml carbenicillin to kill the excess of bacteria). The plates are sealed with Millipore tape and incubated at 28° C. in the dark for approximately two weeks, after which the calli become visible. The efficiency of protein interference (here the aggregation between the GFP-construct and the RFP-construct) is visualized by checking the expression of GFP, RFP and the co-localization of GFP and RFP under the fluorescence microscope.

Material and Methods Related to Examples 1 and 2

Constructs, Cells and Media

The interferor molecules were cloned into the vector pETM60 (gift from G. Stier, EMBL). This vector is under RNA polymerase T7 control (the T7 RNA polymerase is under the control of regulatory elements from the *E. coli* lac operon), confers kanamycin resistance and provides an N-terminal expression tag of six histidines followed by NusA. A series of overlapping oligos coding for the sequence of interferor part B were used to create a "synthetic gene" by PCR. This gene was ligated into pETM60 via NcoI and BamHI restriction sites. Interferor genes were created by PCR of interferor part B, using a long, anti-coding oligo to include the sequence for the flexible linker and the protein specific self-association region (the bait) at the C-terminus. These were ligated into pETM60 via NcoI and BamHI restriction sites. All oligos were purchased from Sigma-Genosys, all restriction enzymes from Fermentas, and ligations were performed using the Quick Ligation Kit from Roche.

Chemically competent BL21 (DE3) cells were produced in house and transformed following standard protocols. Standard LB-agar plates were prepared, and all agar plates contained 50 µg/mL kanamycin. M9 complete plates were prepared by supplementing standard M9 media with all 20 amino acids (50 µg/mL) and nucleotides adenine, guanine, uracil and xanthine (20 µg/mL). M9 select plates were identical to M9 complete in all but one amino acid. To control for possible amino acid degradation upon storage, plates were prepared one day before use. LB was prepared following standard protocols and kanamycin was included at 50 µg/mL. All amino acids were purchased from Sigma; kanamycin and IPTG from Duchefa.

Protocols

BL21 (DE3) cells were transformed with the expression constructs, plated on LB-agar plus kanamycin and incubated at 37° C. overnight. A single colony was used to inoculate 10 mL LB plus kanamycin and this was grown overnight at 37° C., shaking. The following day, this culture was used to inoculate 10 mL LB plus kanamycin 1:100 and this was grown until an OD600 of 0.6 was obtained. Cultures were then divided in two; IPTG (50 µM) was added to one culture to induce interferor expression, and both cultures were further incubated at 37° C. for the desired expression time. Cells were then harvested by centrifugation and washed twice (by resuspension and centrifugation) with salt solution (0.85% w/v NaCl). Cells were then resuspended in salt solution to give a final OD600 of 0.05, and 200 µL of this cell suspension was plated onto agar plates. Agar plates were incubated at 37° C. overnight and colony growth was noted the following day. Where necessary, colonies were picked with a sterile tooth pick onto fresh agar plates.

TABLES

TABLE 1

Summary of the dose-response effects of different VEGF interferor molecules (used in Example 8) on zebra fish vasculature

| | | 48 hpf embryos with indicated vascular phenotype | | | | | |
|---|---|---|---|---|---|---|---|
| Interferor | Conc. | % of affected embryos | Thin Dorsal Aorta | Abnormal PCV | Delay in ISV sprouting | Abnormal VP | Number of embryos analyzed |
| E | 50 µM | — | — | — | — | — | 10 |
| A | 2.5 µM | 80% | 20% | 40% | 20% | 20% | 10 |

TABLE 1-continued

Summary of the dose-response effects of different VEGF interferor molecules (used in Example 8) on zebra fish vasculature

| | | 48 hpf embryos with indicated vascular phenotype | | | | | |
|---|---|---|---|---|---|---|---|
| Interferor | Conc. | % of affected embryos | Thin Dorsal Aorta | Abnormal PCV | Delay in ISV sprouting | Abnormal VP | Number of embryos analyzed |
| B | 1 µM | most embryos died | | | | | 10 |
| C | 2 µM | 80% | 20% | 20% | 20% | 20% | 10 |
| D | 2.5 µM | most embryos died | | | | | 10 |

TABLE 2 proteins derived from Arabidopsis thaliana, identified self-association regions and corresponding TANGO scores

| Gene | TANGO score | self-association region |
|---|---|---|
| AtFH5 | 95.7956 | VFWLILFSGLLVITL (SEQ ID NO: 45) |
| AtFH5 | 75.3155 | IIIAVVVTAVSTFLLAALFFLC (SEQ ID NO: 46) |
| AtFH6 | 80.8913 | FFFFYIFFSVSVSS (SEQ ID NO: 47) |
| AtFH6 | 64.3993 | AIVISVGIVTLGMLSALAFFLY (SEQ ID NO: 48) |
| AtMAP65-3 | 55.9959 | QFIVVM (SEQ ID NO: 49) |
| AURORA1 | 51.1964 | YLILEYAA (SEQ ID NO: 50) |
| AURORA1 | 19.4128 | YGYFY (SEQ ID NO: 51) |
| AURORA2 | 35.8169 | VYLILEYAVRG (SEQ ID NO: 52) |
| AURORA2 | 20.1483 | YGYFY (SEQ ID NO: 51) |
| AURORA3 | 78.0306 | IFLIL (SEQ ID NO: 53) |
| AURORA3 | 16.6145 | FGWF (SEQ ID NO: 54) |
| TPLATE | 73.2511 | SIIAILTLW (SEQ ID NO: 55) |
| TPLATE | 20.4469 | GFWVQVLYYPF (SEQ ID NO: 56) |
| TPLATE | 16.3765 | IWTIA (SEQ ID NO: 57) |

REFERENCES

The Contents of the Entirety of Each of Which are Incorporated Herein by this Reference 1. Dobson C. M. Protein-misfolding diseases: Getting out of shape. *Nature* 418:729-730 (2002).
2. Dobson C. M. Principles of protein folding, misfolding and aggregation. *Semin. Cell Dev. Biol* 15:3-16 (2004).
3. Nelson R. et al. Structure of the cross-beta spine of amyloid-like fibrils. *Nature* 435:773-8 (2005).
4. Makin O. S., E. Atkins, P. Sikorski, J. Johansson and L. C. Serpell. Molecular basis for amyloid fibril formation and stability. *Proc. Natl. Acad. Sci. U.S.A.* 102:315-20 (2005).
5. Hamada D., I. Yanagihara and K. Tsumoto. Engineering amyloidogenicity towards the development of nanofibrillar materials. *Trends Biotechnol.* 22:93-7 (2004).
6. Fernandez-Escamilla A. M., F. Rousseau, J. Schymkowitz, and L. Serrano. Prediction of sequence-dependent and mutational effects on the aggregation of peptides and proteins. *Nat. Biotechnol.* 22:1302-6 (2004).
7. Chiti F., M. Stefani, N. Taddei, G. Ramponi, and C. M. Dobson. Rationalization of the effects of mutations on peptide and protein aggregation rates. *Nature* 424:805-8 (2003).
8. Pawar A. P. et al. Prediction of "aggregation-prone" and "aggregation-susceptible" regions in proteins associated with neurodegenerative diseases. *J. Mol. Biol.* 350:379-92 (2005).
9. Lopez de la Paz M. and L. Serrano. Sequence determinants of amyloid fibril formation. *Proc. Natl. Acad. Sci. U.S.A.* 101:87-92 (2004).
10. Linding R., J. Schymkowitz, F. Rousseau, F. Diella and L. Serrano. A comparative study of the relationship between protein structure and beta-aggregation in globular and intrinsically disordered proteins. *J. Mol. Biol.* 342:345-53 (2004).
11. Clark L. A. Protein aggregation determinants from a simplified model: cooperative folders resist aggregation. *Protein Sci.* 14:653-62 (2005).
12. Barral J. M., S. A. Broadley, G. Schaffar and F. U. Hartl. Roles of molecular chaperones in protein misfolding diseases. *Semin. Cell Dev. Biol.* 15:17-29 (2004).
13. De Marco V., G. Stier, S. Blandin and A. de Marco. The solubility and stability of recombinant proteins are increased by their fusion to NusA. *Biochem. Biophys. Res. Commun.* 322-766-71 (2004).
14. Houry W. A., D. Frishman, C. Eckerskorn, F. Lottspeich and F. U. Hartl. Identification of in vivo substrates of the chaperonin GroEL. *Nature* 402:147-54 (1999).
15. Bairoch A. et al. The Universal Protein Resource (UniProt), *Nucleic Acids Res.* 33, D154-9 (2005).
16. Kopp J. and T. Schwede. The SWISS-MODEL Repository of annotated three-dimensional protein structure homology models. *Nucleic Acids Res.* 32, D230-4 (2004).
17. Guex N. and M. C. Peitsch. SWISS-MODEL and the Swiss-PdbViewer: An environment for comparative protein modeling. *Electrophoresis* 18:2714-2723 (1997).

What is claimed is:

1. A method for inhibiting a biological function of a protein, the method comprising:
contacting said protein with a non-naturally occurring molecule, wherein:
said protein comprises a first β-aggregating region, said non-naturally occurring molecule consisting of 5 to 30 contiguous amino acids, said 5 to 30 contiguous amino acids comprising a second β-aggregating region, and said first and second β-aggregating regions are identical,
cross-beta aggregation occurs between the protein and the non-naturally occurring molecule via the formation of intermolecular beta-sheets between said first and second β-aggregating regions,
the non-naturally occurring molecule is a polypeptide, and
said biological function is inhibited through the cross-beta aggregation, wherein said non-naturally occurring molecule is optionally fused to a solubilizing moiety, and wherein, if the protein is inhibited in a multicellular organism, the contacting between the protein and the non-naturally occurring molecule is by administering the non-naturally occurring molecule to the multicellular organism.

2. The method according to claim 1, wherein said non-naturally occurring molecule is fused to a solubilizing moiety that prevents aggregation of said second β-aggregating region, wherein said moiety is biotin, a peptide, a protein domain or an agarose bead.

3. The method according to claim 2, wherein said moiety is a peptide, a protein domain or an agarose bead.

4. The method according to claim 2, wherein a linker is present between said second β-aggregating region and said moiety.

5. The method according to claim 4, wherein said linker is a polypeptide.

6. The method according to claim 1, wherein said protein is inhibited in an isolated cell, an isolated cell line, or a unicellular organism and said non-naturally occurring molecule is a polypeptide encoded by a nucleotide sequence present on a recombinant vector and which, upon transformation to said isolated cell, isolated cell line, or unicellular organism, produces said polypeptide in said isolated cell, isolated cell line, or unicellular organism.

7. The method according to claim 2, wherein the second β-aggregating region consists of 5 to 20 contiguous amino acids.

8. The method according to claim 7, wherein a linker is present between the second β-aggregating region and the moiety.

9. The method according to claim 8 wherein the linker is a polypeptide.

10. The method according to claim 1, wherein the first β-aggregating region in said protein is fully buried in the protein and becomes solvent-exposed to allow cross-beta aggregation.

11. The method according to claim 2, wherein the first β-aggregating region in said protein is fully buried in the protein and becomes solvent-exposed to allow cross-beta aggregation.

\* \* \* \* \*